US007816516B2

(12) United States Patent
Sommermeyer et al.

(10) Patent No.: US 7,816,516 B2
(45) Date of Patent: Oct. 19, 2010

(54) CONJUGATES OF HYDROXYALKYL STARCH AND AN ACTIVE AGENT

(75) Inventors: Klaus Sommermeyer, Rosbach (DE); Wolfram Eichner, Butzbach (DE); Sven Frie, Bramois (CH); Cornelius Jungheinrich, Bad Homburg (DE); Roland Scharpf, Ranstadt (DE); Katharina Lutterbeck, Friedberg (DE); Jurgen Hemberger, Aschaffenburg (DE); Michele Orlando, The Hague (NL)

(73) Assignee: Fresenius Kabi Deutschland GmbH, Bad Homburg v.d.H. (DE)

( * ) Notice: Subject to any disclaimer, the term of this patent is extended or adjusted under 35 U.S.C. 154(b) by 736 days.

(21) Appl. No.: 10/472,002

(22) PCT Filed: Mar. 15, 2002

(86) PCT No.: PCT/EP02/02928

§ 371 (c)(1),
(2), (4) Date: Sep. 22, 2004

(87) PCT Pub. No.: WO02/080979

PCT Pub. Date: Oct. 17, 2002

(65) Prior Publication Data

US 2005/0063943 A1    Mar. 24, 2005

(30) Foreign Application Priority Data

Mar. 16, 2001  (DE) ................ 101 12 825

(51) Int. Cl.
*C08B 31/18* (2006.01)
*A61K 31/718* (2006.01)
(52) U.S. Cl. .................. 536/124; 536/111; 514/60
(58) Field of Classification Search .......... 536/124, 536/111; 514/60
See application file for complete search history.

(56) References Cited

U.S. PATENT DOCUMENTS

| 3,191,291 | A | 6/1965 | Maier |
|---|---|---|---|
| 4,001,200 | A | 1/1977 | Bonsen et al. |
| 4,001,401 | A | 1/1977 | Bonsen et al. |
| 4,053,590 | A | 10/1977 | Bonsen et al. |
| 4,061,736 | A | 12/1977 | Bonsen et al. |
| 4,064,118 | A | 12/1977 | Wong |
| 4,125,492 | A | 11/1978 | Cuatrecasas et al. |
| 4,179,337 | A | 12/1979 | Davis et al. |
| 4,261,973 | A | 4/1981 | Lee et al. |
| 4,412,989 | A | 11/1983 | Iwashita et al. |
| 4,667,016 | A | 5/1987 | Lai et al. |
| 4,703,008 | A | 10/1987 | Lin |
| 4,766,106 | A | 8/1988 | Katre et al. |
| 4,847,325 | A | 7/1989 | Shadle et al. |
| 4,863,964 | A | 9/1989 | Hedlund et al. |
| 4,900,780 | A | 2/1990 | Cerny |
| 4,904,584 | A | 2/1990 | Shaw |
| 4,925,677 | A * | 5/1990 | Feijen .................. 424/484 |
| 4,952,496 | A | 8/1990 | Studier et al. |
| 5,068,321 | A | 11/1991 | Buysch et al. |
| 5,079,337 | A | 1/1992 | Leonard et al. |
| 5,214,132 | A | 5/1993 | Kuga et al. |
| 5,217,998 | A | 6/1993 | Hedlund et al. |
| 5,218,092 | A | 6/1993 | Sasaki et al. |
| 5,218,108 | A | 6/1993 | Sommermeyer et al. |
| 5,281,698 | A | 1/1994 | Nitecki |
| 5,362,853 | A | 11/1994 | Kuga et al. |
| 5,470,843 | A | 11/1995 | Stahl et al. |
| 5,484,903 | A | 1/1996 | Szablikowski et al. |
| 5,543,332 | A | 8/1996 | Lihme et al. |
| 5,581,476 | A | 12/1996 | Osslund |
| 5,622,718 | A | 4/1997 | Al-Shamkhani et al. |
| 5,723,589 | A | 3/1998 | Miljkovic et al. |
| 5,876,980 | A | 3/1999 | DeFrees et al. |
| 5,952,347 | A | 9/1999 | Arison et al. |
| 6,011,008 | A | 1/2000 | Domb et al. |
| 6,083,909 | A | 7/2000 | Sommermeyer et al. |
| 6,261,800 | B1 | 7/2001 | Nikolics et al. |
| 6,299,881 | B1 * | 10/2001 | Lees et al. .............. 424/194.1 |
| 6,340,746 | B1 | 1/2002 | Roberts et al. |
| 6,375,846 | B1 | 4/2002 | Jarrett et al. |

(Continued)

FOREIGN PATENT DOCUMENTS

| CA | 2 233 725 | 9/1999 |
|---|---|---|
| CA | 2233725 A1 * | 9/1999 |
| CA | 2 441 442 | 9/2003 |
| CA | 2 478 478 | 1/2004 |
| CA | 2 478 480 | 1/2004 |

(Continued)

OTHER PUBLICATIONS

Sakai et al., "Synthesis and Physiochemical Characterization of a Series of Hemoglobin-Based Oxygen Carriers", 2000, Bioconjugate Chemistry, 11, p. 56-64.*

(Continued)

*Primary Examiner*—Shaojia Anna Jiang
*Assistant Examiner*—Jonathan S Lau
(74) *Attorney, Agent, or Firm*—Fish & Richardson P.C.

(57) ABSTRACT

The invention relates to compounds, comprising a conjugate of hydroxyalkyl starch (HAS) and an active agent, whereby the hydroxyalkyl starch is either directly covalently bonded to the active agent, or by means of a linker. The invention further relates to methods for the production of a covalent HAS-active agent conjugate, whereby HAS and an active agent are reacted in a reaction medium, characterised in that the reaction medium is water or a mixture of water and an organic solvent, comprising at least 10 wt. % water.

14 Claims, 12 Drawing Sheets

U.S. PATENT DOCUMENTS

| | | |
|---|---|---|
| 6,500,930 B2 | 12/2002 | Adamson |
| 6,555,660 B2 | 4/2003 | Nissen et al. |
| 6,586,398 B1 | 7/2003 | Kinstler et al. |
| 6,596,861 B1 | 7/2003 | Moreau |
| 6,875,594 B2 | 4/2005 | Muir et al. |
| 7,115,576 B2 | 10/2006 | Sommermeyer |
| 7,179,617 B2 | 2/2007 | DeFrees et al. |
| 7,285,661 B2 | 10/2007 | Sommermeyer et al. |
| 2004/0043446 A1 | 3/2004 | DeFrees et al. |
| 2004/0180858 A1 | 9/2004 | Sommermeyer |
| 2005/0063943 A1 | 3/2005 | Sommermeyer et al. |
| 2005/0181985 A1 | 8/2005 | Hemberger et al. |
| 2005/0238723 A1 | 10/2005 | Zander et al. |
| 2006/0019877 A1 | 1/2006 | Conradt et al. |
| 2006/0217293 A1 | 9/2006 | Orlando et al. |

FOREIGN PATENT DOCUMENTS

| | | |
|---|---|---|
| DE | 22 33 977 | 2/1973 |
| DE | 26 16 086 | 11/1977 |
| DE | 26 16 086.1 | 11/1977 |
| DE | 30 29 307 | 3/1982 |
| DE | 30 29 307 A1 | 3/1982 |
| DE | 26 46 854 | 5/1989 |
| DE | 38 36 600 | 3/1990 |
| DE | 279 486 | 6/1990 |
| DE | 41 30 807 | 3/1993 |
| DE | 26 07 706 | 5/1993 |
| DE | 196 28 705 | 1/1998 |
| DE | 198 08 079 | 8/1999 |
| DE | 101 12 825 | 2/2002 |
| DE | 100 41 541 | 3/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 218 825 | 4/1987 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 338 916 | 10/1989 |
| EP | 0 402 724 | 6/1990 |
| EP | 0 138 572 | 7/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0 640 619 | 3/1995 |
| EP | 0 646 130 | 4/1995 |
| EP | 0 418 523 | 6/1995 |
| EP | 0 668 351 | 8/1995 |
| EP | 0 809 996 | 5/1996 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| EP | 1 064 951 | 8/2007 |
| FR | 2 378 094 | 8/1978 |
| GB | 1 419 080 | 12/1975 |
| GB | 1 549 246 | 10/1976 |
| JP | 10-287554 | 10/1998 |
| WO | WO 80/02374 | 11/1980 |
| WO | WO 90/07939 | 7/1990 |
| WO | WO 90/15628 | 12/1990 |
| WO | WO 92/11037 | 7/1992 |
| WO | WO 93/23062 | 11/1993 |
| WO | WO 94/01483 | 1/1994 |
| WO | WO 94/05332 | 3/1994 |
| WO | WO 94/07536 | 4/1994 |
| WO | 94/13697 | 6/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | 98/01158 | 1/1998 |
| WO | WO 98/01158 | 1/1998 |
| WO | WO 98/08856 | 3/1998 |
| WO | 98/20905 | 5/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | 99/49897 | 10/1999 |
| WO | WO 99/49897 | 10/1999 |
| WO | WO 00/78355 | 12/2000 |
| WO | WO 01/70272 | 9/2001 |
| WO | WO 01/83522 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/080979 | 10/2002 |
| WO | WO 03/000738 | 1/2003 |
| WO | WO 03/031464 | 4/2003 |
| WO | WO 03/031581 | 4/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | WO 2005/074993 | 8/2005 |
| WO | WO 2005/092390 | 10/2005 |

WO    WO 2006/108052    10/2006

OTHER PUBLICATIONS

Definition of dimethyl sulfoxide, The Merck Index, 2006, Merck & Co., 14th edition, accessed online http://themerckindex.cambridgesoft.com/TheMercklndex/index.asp on Sep. 4, 2007.*
Liu et al. Biochimica et Biophysica Acta, 1998, 1385, p. 53-60.*
Boyer et al. Tetrahedron, 2000, 56, p. 303-307.*
Lewis et al. J. Chem. Soc., Perkins Trans. 1, 1998, p. 2481-2484.*
Lewis et al. Tetrahedron letters, 1998, 39, p. 9559-9562.*
Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.
Alayash and Cashon, "Hemoglobin and free radicals: implications for the development of a safe blood substitute," *Molec. Med. Today*, 1995, 1(3):122-127.
Ashwell, "Carbohydrate Antigens: Coupling of Carbohydrates to Proteins by a Mixed Anhydride Reaction," *Meth. Enzymol.*, 1972, 28:219-222.
Avigad, "A Simple Spectrophotometric Determination of Formaldehyde and Other Aldehydes:. Application to Periodate-Oxidized Glycol Systems," *Anal. Biochem.*, 1983, 134:499-504.
Baldwin et al., "Synthesis of Polymer-Bound Hemoglobin Samples," *Tetrahedron*, 1981, 37:1723-1726.
Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.
Barbone et al., "Reticulocyte measurements as a bioassay for erythropoietin," *J. Pharm. Biomed. Anal.*, 1994, 12(4):515-522.
Barstrom et al., "New derivatives of reducing oligosaccharides and their use in enzymatic reactions: efficient synthesis of sialyl Lewis a and sialyl dimeric Lewis x glycoconjugates," *Carbohydr. Res.* 2000, 328:525-531.
Bauer et al., "Synthesis of w—(Aminooxy)alkanethiols," *J. Org. Chem.*, 1965, 30:949-951.
Bauer and Suresh, "S[w-(Aminoöxy)alkyl]isothiuronium Salts, w,w'-Bis(aminoöxy)alkanes and Related Compounds," *J. Org. Chem.*, 1963, 28:1604-1608.
Bendele et al., "Short Communication: Renal Tubular Vacuolation in Animals Treated with Polyethylene-Glycol-Conjugated Proteins," *Toxicol. Sci.*, 1998, 42:152-157.
Benesch, "Bis(pyridoxal) Polyphosphates as Specific Intramolecular Cross-Linking Agents for Hemoglobin," *Meth. Enzymol.*, 1994, 231:267-274.
Bepperling et al., "HES 130/0.4, a new HES specification: tissue storage after multiple infusions in rats," *Crit. Care*, 1999, 3(suppl 1):p. 153.
Berger et al., "Galactosyltransferase-dependent sialylation of complex and *endo-N*-acetylglucosaminidase H-treated core *N*-glycans in vitro," *FEBS Lett.*, 1986, 203(1):64-68.
Black et al., "*N*-Bromoacetyl-glycopyranosylamines as affinity labels for a β-glucosidase and a cellulase," *Carbohydr. Res.*, 1993, 250:195-202.
Bobbitt, "Periodate Oxidation of Carbohydrates," *Carbohydr. Chem.*, 1956, 11:1-41.
Boissel et al., "Erythropoietin Structure-Function Relationships. Mutant proteins that test a model of tertiary structure," *J. Biol. Chem.*, 1993, 268(21):15983-15993.
Boturyn et al., "Synthesis of Fluorescent Probes for the Detection of Abasic Sites in DNA," *Tetrahedron*, 1997, 53(15):5485-5492.
Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.
Bronzino, *The Biomedical Engineering Handbook*, CRC Press, USA, Salem, 1995, (TOC only).
Bunn & Jandl, "The Renal Handling of Hemoglobin. II. Catabolism," *J. Exp. Med.*, 1967, 129:925-934.
Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation," *Glycoconj. J.*, 1999, 16:691-695.
Cabacungan et al., "Amine Boranes as Alternative Reducing Agents for Reductive Alkylation of Proteins," *Anal. Biochem.*, 1982, 124:272-278.
Carlsson et al., "Protein Thiolation and Reversible Protein-Protein Conjugation," *Biochem J.*, 1978, 173:723-737.
Cerami, "Beyond Erythropoiesis: Novel Applications for Recombinant Human Erythropoietin," *Semin. Hematol.*, 2001, 38:(3 Suppl 7):33-39.
Cerny et al., "A Hydroxyethyl Starch-Hemoglobin Polymer as a Blood Substitute," *Clinical Hemorheology*, 1982, 2(4):355-365.
Chamow et al., "Conjugation of Soluble CD4 without Loss of Biological Activity via a Novel Carbohydrate-directed Cross-linking Reagent," *J. Biol. Chem.*, 1992, 267(22):15916-15922.
Chang, "Blood Substitutes Based on Modified Hemoglobin Prepared by Encapsulation or Crosslinking: An Overview," *Biomat., Art. Cells & Immob. Biotech.*, 1992, 20:159-179.
Chagnon et al., "Murine renal cell carcinoma: evaluation of a dendritic-cell tumour vaccine," *BJU Int.*, 2001, 88:418-424.
Chaplin, "Monosaccharides," *Carbohydrate analysis: a pratical approach*, 1996, Chaplin and Kennedy (eds.), Chapter 1, "Oligosaccharides," pp. 37-54.
Chaplin, "A Rapid and Sensitive Method for the Analysis of Carbohydrate Components in Glycoproteins Using Gas-Liquid Chromatography," *Anal. Biochem.*, 1982, 123:336-341.
Chapman et al., "Therapeutic antibody fragments with prolonged in vivo half-lives," *Nature Biotech.*, 1999, 17:780-783.
Chow et al., "In vitro Induction of apoptosis of neoplastic cells in low-grade non-Hodgkin's lymphomas using combinations of established cytotoxic drugs with bendamustine," *Haematologica*, 2001, 86:485-493.
Chu et al., "Further Studies on the Immunogenicity of *Haemophilus influenzae* Type b and Pneumococcal Type 6A Polysaccharide-Protein Conjugates," *Infect. Immun.*, 1983, 40:245-256.
Cumber et al., "Preparation of Antibody-Toxin Conjugates," *Meth. Enzymol.*, 1985, 112:207-225.
Delgado et al., "The Uses and Properties of PEG-Linked Proteins," *Crit. Rev. Ther. Drug Carrier Syst.*, 1992, 9(3,4):249-304.
Delorme et al., "Role of Glycosylation on the Secretion and Biological Activity of Erythropoietin," *Biochemistry*, 1992, 31(41):9871-9876.
Dittmar et al., "Human Glycoproteins and Derived Variants from Recombinant Mammalian Cell Lines," *Advances in Protein Design*, 1989, 12:145-156.
Dorner et al., "Increased Synthesis of Secreted Proteins Induces Expression of Glucose-regulated Proteins in Butyrate-treated Chinese Hamster Ovary Cells," *J. Biol. Chem.*, 1989, 264(34):20602-20607.
Dowling and Russell, "Pharmacokinetics of a long-acting oxytetracycline-polyethylene glycol formulation in horses," *J. Vet. Pharmacol. Therap.*, 2000, 23:107-110.
Dreborg and œkerblom, "Immunotherapy with Monomethoxypolyethylene Glycol Modified Allergens," *Crit. Rev. Ther. Drug Carrier Syst.*, 1990, 6(4):315-365.
Edmunds et al., "Transgenically Produced Human Antithrombin: Structural and Functional Comparison to Human Plasma-Derived Antithrombin," *Blood*, 1998, 91(12):4561-4571.
Blum et al., "Improved silver staining of plant proteins, RNA and DNA in polyacrylamide gels," *Electrophoresis*, 1987, 8:93-99.
Elliott et al., "Mapping of the Active Site of Recombinant Human Erythropoietin," *Blood*, 1997, 89(2): 493-502.
European Pharmacopoeia, "Erythropoietin Concentrated Solution," 3rd Edition, 2000, Monography, pp. 655-660.
European Pharmacopoeia, "Erythropoietin Concentrated Solution," 4th Edition, 2002, Monography, pp. 1123-1128.
Fernández-Santana et al., "Conjugation of 5-azido-3-oxapentyl glycosides with thiolated proteins through the use of thiophilic derivatives," *Glycoconj. J.*, 1998, 15:549-553.
Fibi et al., "Evidence for the Location of the Receptor-Binding Site of Human Erythropoietin at the Carboxyl-Terminal Domain," *Blood*, 1991, 77(6):1203-1210.

Fibi et al., "N- and O-Glycosylation Muteins of Recombinant Human Erythropoietin Secreted From BHK-21 Cells," *Blood*, 1995, 85(5):1229-1236.

Fissekis et al., "*N*-Pantyol-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Gaertner and Offord, "Site-Specific Attachment of Functionalized Poly(ethylene glycol) to the Amino Terminus of Proteins," *Bioconjugate Chemistry*, 1996, 7(1):38-44.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Gonzalez Lio and Thiem, "Chemoenzymatic synthesis of spacer-linked oligosaccharides for the preparation of neoglycoproteins," *Carbohydr. Res.*, 1999, 317:180-190.

Gould et al., "The Development of Hemoglobin Solutions as Red Cell Substitutes: Hemoglobin Solutions," *Transfus. Sci.*, 1995, 16:5-17.

Grabenhorst et al., "Construction of stable BHK-21 cells coexpressing human secretory glycoproteins and human Gal(B1-4)GlcNAc-R α2,6-sialyltransferase: α2,6-Linked NeuAc is preferentially attached to the Gal(β1-4)GlcNAc(β1-2)Man(α1-3)-branch of diantennary oligosaccharides from secreted recombinant β-trace protein," *Eur. J. Biochem.*, 1995, 232:718-725.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "In Vivo Specificity of Human α1,3/4-Fucosyltransferases III-VII in the Biosynthesis of Lewis$^x$ Motifs on Complex-type *N*-Glycans. Coexpression studies from BHK-21 cells together with human β-trace protein," *J. Biol. Chem.*, 1998, 273(47):30985-30994.

Grabenhorst et al., "Genetic engineering of recombinant glycoproteins and the glycosylation pathway in mammalian host cells," *Glycoconj J.*, 1999, 16(2):81-97.

Gray, "The Direct Coupling of Oligosaccharides to Proteins and Derivatized Gels," *Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Grimmecke and Brade, "Studies on the reductive amination of 3-deoxy-D-*manno*-octulosonic acid (Kdo)," *Glycoconj. J.*, 1998, 15:555-562.

Habeeb, "Determination of Free Amino Groups in Proteins by Trinitrobenzenesulfonic Acid," *Anal. Biochem.*, 1966, 14:328-336.

Hai et al., "Diaspirin Crosslinked Hemoglobin (DCLHb™) Polymerization," *Art. Cells, Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of β-Lactoglobulin by Conjugation with Carboxymethyl Dextran," *Bioconjug. Chem.*, 2000, 11:84-93.

Herman et al., "Characterization, Formulation, and Stability of Neupogen® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of *N*-Glycans by High-pH Anion-Exchange Chromatography with Pulsed Amperometric Detection," *Anal. Biochem.*, 1992, 203(2):281-289.

Higuchi et al., "Role of Sugar Chains in the Expression of the Biological Activity of Human Erythropoietin," *J. Biol. Chem.*, 1992, 267(11):7703-7709.

Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jia et al., "S-nitrosohaemoglobin: a dynamic activity of blood involved in vascular control," *Nature*, 1996, 380:221-226.

Jones et al., "A convenient synthesis of *N*-(*tert*-butyloxycarbonyl)aminooxy ethers," *Tetrahedron Letters*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Kallin, "Coupling of Oligosaccharides to Proteins Using *p*-Trifluoroacetamidoaniline," *Meth. Enzymol.*, 1994, 242:119-123.

Keaney, Jr. et al., "NO Forms an Adduct with Serum Albumin that Has Endothelium-derived Relaxing Factor-like Properties," *J. Clin. Invest.*, 1993, 91:1582-1589.

Keipert et al., "Functional properties of a new crosslinked hemoglobin designed for use as a red cell substitute," *Transfusion*, 1989, 29:768-773.

Kitamura et al., "Establishment and Characterization of a Unique Human Cell Line That Proliferates Dependently on GM-CSF, IL-3, or Erythropoietin," *J. Cell. Phy.*, 1989, 140:323-334.

Kitamura et al., "Chemical Engineering of the Monoclonal Antibody A7 by Polyethylene Glycol for Targeting Cancer Chemotherapy," *Cancer Res.*, 1991, 51:4310-4315.

Kleine-Tebbe et al., "Allergen Immunotherapy—A Position Paper of the German Society for Allergology and Clinical Immunology," *Pneumologie*, 2001, 55:438-444 (w/English summary).

Klemm et al., "Esterification of Cellulose," *Comprehensive Cellulose Chemistry*, 1998, vol. 2, Wiley-VCH, Weinheim, New York, especially chapter 4.4, pp. 99-207.

Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.

Kojima et al., "Mitomycin C-dextran conjugate: a novel high molecular weight pro-drug of mitomycin C," *J. Pharm. Pharmacol.*, 1980, 32:30-34.

Komatsu et al., "Cloning of granulocyte colony-stimulating factor cDNA from human macrophages and its expression in *Escherichia coli*," *J. Cancer Res.*, 1987, 78(11):1179-1181.

Krantz, "Erythropoietin," *Blood*, 1991, 77(3):419-434.

Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.

Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.

Krystal et al., "Purification of Human Erythropoietin to Homogeneity by a Rapid Five-Step Procedure," *Blood*, 1986, 67(1):71-79.

Kuberan et al., "Preparation and isolation of neoglycoconjugates using biotin-streptavidin complexes," *Glycoconj. J.*, 1999, 16:271-281.

Kurtz and Eckardt, "Assays for Erythropoietin," *Nephron.*, 1989, 51(suppl 1):11-14 (w/English summary).

Larionova et al., "Conjugation of the Bowman-Birk Soybean Proteinase Inhibitor with Hydroxyethylstarch," *Appl. Biochem. Biotech.*, 1997, 62:175-182.

Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.

Leenders et al., "β-Glucuronyl Carbamate Based Pro-moieties Designed for Prodrugs in ADEPT," *Tetrahedron Letters*, 1995, 36(10):1701-1704.

Lees et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," 1990, *J. Cardiovasc. Pharmacol.*, 1990, 16(4):523-528.

Levy et al., "Recombinant Antithrombin: Production and Role in Cardiovascular Disorder," *Sem. Thromb. Hem.*, 2001, 27(4):405-416.

Lin et al., "Cloning and expression of the human erythropoietin gene," *Proc. Natl. Acad. Sci. USA*. 1985, 82:7580-7584.

Lindsey at al., "Porphyrin Building Blocks for Modular Construction of Bioorganic Model Systems," *Tetrahedron*, 1994, 50(30):8941-8968, especially p. 8956.

Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.

Lönngren and Goldstein, "Coupling of Aldobionic Acids to Proteins Using Water-Soluble Carbodiimide," *Meth. Enzvmol.*, 1994, 242:116-118.

Manger et al., "1-$N$-Glycyl β-Oligosaccharide Derivatives as Stable Intermediates for the Formation of Glycoconjugate Probes," *Biochemistry*, 1992, 31:10724-10732.

Manger et al., "Synthesis of 1-$N$-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.

Maout et al., "Hydroxyethylstarch Conjugated to Human Hemoglobin for use in Blood Transfusion: Comparison with Dextran Conjugates," *Carbohydrates and Carbohydrate Polymers—Analysis, Biotechnology, Modification, Antiviral and Other Applications*, 1993, Chapter 12, pp. 132-140.

McMahon et al., "Pharmacokinetics and Effects of Recombinant Human Erythropoietin After Intravenous and Subcutaneous Injections in Healthy Volunteers," *Blood*, 1990, 76(9):1718-1722.

Meinjohanns et al., "Novel sequential solid-phase synthesis of N-linked glycopeptides from natural sources," *J. Chem. Soc., Perkin Trans. 1*, 1998, 1:549-560.

Mikola and Hanninen, "Introduction of Aliphatic Amino and Hydroxy Groups to Keto Steroids Using O-Substituted Hydroxylamines," *Bioconj. Chem.*, 1992, 3(2):182-186.

Minnema et al., "Recombinant human antithrombin III improves survival and attenuates inflammatory responses in baboons lethally challenged with *Escherichia coli*," *Blood* 2000, 95(4):1117-1123.

Miyake et al., "Purification of Human Erythropoietin," *J. Biol. Chem.*, 1977, 252(15):5558-5564.

Montreuil et al., "Hexuronic acids," *Carbohydrate analysis: a practical approach*, 1996, Chaplin and Kennedy (eds.), Chapter 5, pp. 175-204.

Mosbech et al., "Hyposensitization in asthmatics with mPEG-modified and unmodified house dust mite extract," *Allergy*, 1990, 45(2):130-141.

Mosmann, "Rapid Colorimetric Assay for Cellular Growth and Survival: Application to Proliferation and Cytotoxicity Assays," *J. Immunol. Meth.*, 1983, 65:55-63.

Mueller et al., "Recombinant Glycoprotein Product Quality in Proliferation-Controlled BHK-21 Cells," *Biotechnol. Bioeng.*, 1999, 65(5):529-536.

Davis and Flitsch, "A Novel Method for the Specific Glycosylation of Proteins," *Tetrahedron Lett.*, 1991, 32(46):6793-6796.

Nagata et al., "The chromosomal gene structure and two mRNAs for human granulocyte colony-stimulating factor," *EMBO J.*, 1986, 5(3):575-581.

Nagata et al., "Molecular cloning and expression of cDNA for human granulocyte colony-stimulating factor," *Nature*, 1986, 319:415-418.

Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.

Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.

Nimtz et al., "Structural characterization of the oligosaccharide chains of native and crystallized boar seminal plasma spermadhesin PSP-I and PSP-II glycoforms," *Eur. J. Biochem.*, 1999, 265:703-718.

Nimtz et al., "Structures of sialylated oligosaccharides of human erythropoietin expressed in recombinant BHK-21 cells," *Eur. J. Biochem.*, 1993, 213:39-56.

Nimtz et al., "Carbohydrate structures of a human tissue plasminogen activator variant expressed in recombinant Chinese hamster ovary cells," *FEBS Lett.*, 1990, 271:14-18.

Nohynek et al., "Comparison of the potency of glycosylated and nonglycosylated recombinant human granulocyte colony-stimulating factors in neutropenic and nonneutropenic CD rats," *Cancer Chemother Pharmacol.*, 1997, 39:259-266.

Nomura et al., "Pharmacokinetic characteristics and therapeutic effects of mitomycin C-dextran conjugates after intratumoural injection," *J. Controlled Release*, 1998, 52:239-252.

O'Shannessy and Wilchek, "Immobilization of Glycoconjugates by Their Oligosaccharides: Use of Hydrazido-Derivatized Matrices," *Analytical Biochemistry*, 1990, 191:1.

Pawlowski et al., "A new method of non-cross-linking conjugates of polysaccharides to protein via thioether bonds for the preparation of saccharide-protein conjugate vaccines," *Vaccine*, 1999, 17:1474-1483.

Pazur, "Neutral polysaccharides," *Carbohydrate analysis: a practical approach*, 1996, Chaplin and Kennedy (eds.), Chapter 3, pp. 55-96.

Pedley et al., "The potential for enhanced tumour localization by poly)ethylene glycol) modification of anti-CEA antibody," *Br. J. Cancer*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Peron et al., "Hydroxyethyl starch-induced renal insufficiency after plasma exchange in a patient with polymyositis and liver cirrhosis," *Clin. Nephrol.*, 2001, 55(5):408-411.

*Pharma Business*, Jul./Aug. 2000, pp. 45-60.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Ragupathi et al., "A novel and efficient method for synthetic carbohydrate conjugate vaccine preparation: synthesis of sialyl Tn-KLH conjugate using a 4-(4-$N$-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Reidhaar-Olson et al., "Identification of Residues Critical to the Activity of Human Granulocyte Colony-Stimulating Factor," *Biochemistry*, 1996, 35:9034-9041.

Relihan et al., "Clearance Rate and Effect on Renal Function of Stroma-Free Hemoglobin Following Renal Ischemia," *Ann. Surg.*, 1972, 176(6):700-704.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Rogers et al., "Effects of polymerization on the oxygen carrying and redox properties of diaspirin cross-linked hemoglobin," *Biochim. Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Rose, "Facile Synthesis of Homogeneous Artificial Proteins," *J. Am. Chem. Soc.*, 1994, 116:30-33.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67:(8):1442-1452.

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al., "Synthesis and Physicochemical Characterization of a Series of Hemoglobin-Based Oxygen Carriers: Objective Comparison between Cellular and Acellular Types," *Bioconj. Chem.*, 2000, 11:56-64.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian Journal of Chemistry*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnology*, 1999, 30:17-25.

Schottelius et al., "Improvement of Pharmacokinetics of Radioiodinated Tyr$^3$-Octreotide by Conjugation with Carbohydrates," *Bioconjugate Chem.*, 2002, 13:1021-1030.

Schröter et al., "Male-specific Modification of Human CD52," *J. Biol. Chem.*, 1999, 274(42):29862-29873.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.

Shah et al., "Characterization of Colony-stimulating Activity Produced by Human Monocytes and Phytohemagglutinin-stimulated Lymphocytes," 1977, *Blood*, 50(5):811-821.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.

Simmons et al., "Potent inhibition of HIV-1 infectivity in macrophages and lymphocytes by a novel CCR5 antagonist," *Science*, 1997, 276:276-279.

Snyder et al., "HbXL99α A hemoglobin derivative that is cross-linked between the α subunits is useful as a blood substitute," *Proc. Natl. Acad. Sci. USA*, 1987, 84:7280-7284.

Shu, "Somogyi Micro Copper Method," *Method in Carbohydride Chemistry*, 1962, 1:383-388.

Song et al., "Toxicity and Antitumor Activity of the Conjugate of Mitomycin C with Carboxymethyl-chitin," *Arch. Pract. Pharm.*, 1993, 53(3):141-147.

Souza et al., "Recombinant human granulocyte colony-stimulating factor: effects on normal and leukemic myeloid cells," *Science*, 1986, 232:61-65.

Soyez et al., "Biological evaluation of mitomycin C bound to a biodegradablepolymeric carrier," *J. Controlled Release*, 1997, 47:71-80.

Spivak and Hogans, "The In Vivo Metabolism of Recombinant Human Erythropoietin in the Rat," *Blood*, 1989, 73:90-99.

Staros, "N-Hydroxysulfosuccinimide Active Esters: Bis(N-hydroxysulfosuccinimide) Esters of Two Dicarboxylic Acids Are Hydrophilic, Membrane-Impermeant, Protein Cross-Linkers," *Biochemistry*, 1982, 21:3950-3955.

Sunamoto and Iwamoto, "Protein-Coated and Polysaccharide-Coated Liposomes as Drug Carriers," *CRC Critical Review in Therapeutic Drug Carrier Systems*, 1986, 2:117-136.

Sytkowski et al., "Human erythropoietin dimers with markedly enhanced in vivo activity," *Proc. Natl. Acad. Sci. USA*, 1998, 95(3):1184-1188.

Sytkowski et al., "An Erythropoietin Fusion Protein Comprised of Identical Repeating Domains Exhibits Enhanced Biological Properties," *J. Biol. Chem.*, 1999, 274(35):24773-24778.

Takeuchi et al., "Relationship between sugar chain structure and biological activity of recombinant human erythropoietin produced in Chinese hamster ovary cells," *Proc. Natl. Acad. Sci. USA*, 1989, 86:7819-7822.

Takeuchi and Kobata, "Structures and functional roles of the sugar chains of human erythropoietin," *Glycobiology*, 1991, 1(4):337-346.

Tam et al., "Soluble Dextran-Hemoglobin Complex as a Potential Blood Substitute," *Proc. Natl. Acad. Sci. USA*, 1976, 73(6):2128-2131.

Tanaka et al., "Pharmacokinetics of recombinant human granulocyte colony-stimulating factor conjugated to polyethylene glycol in rats," *Cancer Research*, 1991, 51:3710-3714.

Thomas et al., "Measuring blood volume with fluorescent-labeled hydroxyethyl starch," *Crit. Care Med.*, 2000, 28(3):627-631.

Thomas, "Carbohydrate Binding Sites," *Meth. Enzymol.*, 1977, 46:362-368.

Thorpe et al., "Blockade of the galactose-binding sites of ricin by its linkage to antibody," *Eur. J. Biochem.*, 1984, 140:63-71.

Toyama et al., "Surface design of SPR-based immunosensor for the effective binding of antigen or antibody in the evanescent field using mixed polymer matrix," *Sensors and Actuators B*, 1998, 52:65-71.

De Velasco et al., "Synthetic Peptides Representing T-Cell Epitopes Act as Carriers in Pneumococcal Polysaccharide Conjugate Vaccines," *Infect. Immun.*, 1995, 63(3):961-968.

Van Patten et al., "Oxidation of Methionine Residues in Antithrombin," *J. Biol. Chem.*, 1999, 274(15):10268-10276.

Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.

Vilaseca et al., "Protein conjugates of defined structure: Synthesis and use of a new carrier molecule," *Bioconjugate Chemistry*, 1993, 4(6):515-520.

Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.

Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).

White and Kennedy, "Oligosaccharides," *Carbohydrate analysis: a practical approach*, 1996, Chaplin and Kennedy (eds.), Chapter 2, pp. 1-36.

Whitesides et al., "Rates of Thiol-Disulfide Interchange Reactions between Mono- and Dithiols and Ellman's Reagent," *J. Org. Chem.*, 1977, 42(2):332-338.

Wong et al., "Analysis of carbohydrate-protein interactions with synthetic N-linked neoglycoconjugate probes," *Biochem. J.*, 1993, 296:817-825.

Wong et al., "Synthetic glycosylation of proteins using N-(β-saccharide) iodoacetamides: applications in site-specific glycosylation and solid-phase enzymic oligosaccharide synthesis," *Biochem. J.*, 1994, 300:843-850.

Wong, *Chemistry of protein conjugation and cross-linking*, 1993, CRCS, Inc. (TOC only).

Xue and Wong; "Preparation of Conjugated Hemoglobins," *Meth. Enzymol.*, 1994, 231:308-322.

Yalpani et al., "Selective Chemical Modifications of Dextran," *J. Polymer Science: Polymer Chemistry Edition*, 1985, 23:1395-1405.

Yamaguchi et al., "Effects of site-directed removal of N-glycosylation sites in human erythropoietin on its production and biological properties," *J. Biol. Chem.*, 1991, 266(30):20434-20439.

Yoshida, "Glycamine Formation via Reductive Amination of Oligosaccharides with Benzylamine," *Meth. Enzymol.*, 1994, 247:55-64.

Zalipsky, "Functionalized Poly(ethylene glycol) for Preparation of Biologically Relevant Conjugates," *Bioconjugate Chem.*, 1995, 6:150-165.

Zara et al., "A Carbohydrate-Directed Heterobifunctional Cross-Linking Reagent for the Synthesis of Immunoconjugates," *Anal. Biochem.*, 1991, 194:156-162.

Zettlmeissl et al., "Characterization of Recombinant Human Antithrombin III Synthesized in Chinese Hamster Ovary Cells," *J. Biol. Chem.*, 1989, 264 (35):21153-21159.

Zhou et al., "Application of capillary electrophoresis, liquid chromatography, electrospray-mass spectrometry and-matrix-assisted laserdesorption/ionization—time of flight—mass spectrometry to the characterization of recombinant human erythropoietin," *Electrophoresis*, 1998, 19(13):2348-2355.

Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.

Zucali and Sulkowski, "Purification of human urinary erythropoietin on controlled-pore glass and silicic acid," *Exp. Hematol.*, 1985, 13(3):833-837.

Thomas et al., "Measuring blood volume with fluorescent-labeled hydroxyethyl starch," *Crit. Care Med.*, 2000, 28(3):627-631.

International Search Report issued Apr. 24, 2003 in International Application No. PCT/EP02/02928 (WO 02/080979) and English translation thereof.

Cerny et al., "A Hydroxyethyl Starch-Hemoglobin Polymer as a Blood Substitute", *Clinical Hemorheology*, vol. 2, No. 4, pp. 355-365 (1982).

Lesnefsky et al., "High-Dose Iron-Chelator Therapy During Reperfusion with Deferoxamine-Hydroxyethyl Starch Conjugate Fails to Reduce Canine Infarct Size", *Journal of Cardiovascular Pharmacology*, vol. 16, No. 4, pp. 523-528 (1990).

Maout et al., "Hydroxyethylstarch Conjugated to Human Hemoglobin for use in Blood Transfusion: Comparison with Dextran Conjugates", *Carbohydrates and Carbohydrate Polymers—Analysis, Biotechnology, Modification, Antiviral and Other Applications*, pp. 132-140 (1993).

Richter et al., "Antibodies Against Hydrokyethylstarch Produced in Rabbits by Immunization with a Protein-Hydroxyethylstarch Conjugate", *International Archives of Allergy and Applied Immunology*, vol. 52, No. 1-4, pp. 307-314 (1976).

Wong, Chemical Dictionary Entry Concerning Carbohydrates, *Chemistry of Protein Conjugation and Cross-Linking*, 1993, CRCS, Inc., 6 pages including English-language Abstract.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.

Schmoll et al. (eds.), "Summary of Basics of Oncology and Current Therapeutic Approaches," *Compendium for Internistic Oncology*, 1996, Table of Contents with English Summary.

Sommermeyer et al., "Hydroxyethylstarch for Clinical Application: Physical and Chemical Characterisation," *Krankenhauspharmazie*, 1987, 8:271-278.

Klimek et al., "Specific Immunotherapy (Hyposensibilisation)," *Allergologie und Umweltmedizin*, Chapter 15, pp. 157-195.

Staab, "New Methods in Preparatory Organic Chemistry IV. Synthesis using heterocyclic amides (azolides)," *Angew. Chem.*, 1962, 74(12):407-422.

Stille et al., "Atherosclerosis as Consequence of Chronic Infection by Chlamydia Pneumoniae," *Herz*, 1998, 23:185-192 (w/English summary).

Sadrzadeh et al., "The Long-Acting Parenteral Iron Chelator, Hydroxyethyl Starch-Deferoxamine, Fails to Protect Against Alcohol-Induced Liver Injury in Rats", *Journal of Pharmacology and Experimental Therapeutics*, vol. 280, No. 2, pp. 1038-1042 (1997).

Sakai et al., "Synthesis and Physicochemical Characterization of a Series of Hemoglobin-Based Oxygen Carriers: Objective Comparison Between Cellular and Acellular Types", *Bioconjugate Chemistry*, vol. 11, No. 1, pp. 56-64 (2000).

Toyama et al., "Surface Design of SPR-based immunosensor for the effective binding of antigen or antibody in the evanescent field using mixed polymer matrix", *Sensors and Actuators B*, vol. 52, Issues 1-2, pp. 65-71 (1998).

Adamczyk and Fishpaugh, "A Solid Supported Synthesis of Thiol Esters," *Tetrahedron Lett.*, 1996, 37(25):4305-4308.

Aly et al., "Hemophilia A due to mutations that create new N-glycosylation sites," *Proc. Natl. Acad. Sci. USA*, 1992, 89:4933-4937.

Andersson et al., "Isolation and characterization of human factor VIII: Molecular forms in commercial factor VIII concentrate, cryoprecipitate, and plasma," *Proc. Natl. Acad. Sci. USA*, 1986, 83:2979-2983.

Armitage, "Emerging Applications of Recombinant Human Granulocyte-Macrophage Colony-Stimulating Factor," *Blood*, 1998, 92(12):4491-4508.

Balland et al., "Characterisation of two differently processed forms of human recombinant factor IX synthesised in CHO cells transformed with a polycistronic vector," *Eur. J. Biochem.*, 1988, 172(3):565-572.

Bauer and Rosenberg, "Role of Antithrombin III as a Regulator of In Vivo Coagulation," *Semin Hematol.*, 1991, 28:10-18.

Berg et al., "Engineering the proteolytic specificity of activated protein C improves its pharmacological properties," *Proc. Natl. Acad. Sci. USA*, 2003, 100(8):4423-4428.

Bhattacharyya et al., "Recombinant Factor VIII for Haemophilia An Overview of Production Technologies," *CRIPS*, 2003, 4(3):2-8.

Björk and Danielsson, "Antithrombin and related inhibitors of coagulation proteinases," *Proteinase Inhibitors*, 1986, Chapter 17, pp. 489-513.

Boorsma et al., "Bioprocess Applications of a Sindbis Virus-Based Temperature-Inducible Expression System," *Biotech. Bioeng.*, 2002, 79(6): 602-609.

Carrell et al., "Human $\alpha_1$-antitrypsin: carbohydrate attachment and sequence homology," *FEBS Lett.*, 1981, 135(2):301-303.

Carrell et al., "Structural Mobility of Antithrombin and its Modulation by Heparin," *Thromb. Haemost.*, 1997, 78:516-519.

Carver et al., "Expression of human α1 antitrypsin in transgenic sheep," *Cytotechnology*, 1992, 9:77-84.

Castillo et al., "Sensitive Substrates for Human Leukocyte and Porcine Pancreatic Elastase: A Study of the Merits of Various Chromophoric and Fluorogenic Leaving Groups in Assays for Serine Proteases," *Anal. Biochem.*, 1979, 99:53-64.

Cebon et al., "Granulocyte-Macrophage Colony Stimulating Factor from Human Lymphocytes. The effect of glycosylation on receptor binding and biological activity," *J. Biol. Chem.*, 1990, 265(8):4483-4491.

Chamow and Ashkenazi, *Antibody Fusion Proteins*, 1999, Wiley & Sons, Inc. (TOC Only).

Chan et al., "Preparation of O-esters from the corresponding thiol esters: tert-butyl cyclohexanecarboxylate," *Organic Syntheses, Coll.*, 1990, 7:87-93.

Chen et al., "Purification of α₁ Proteinase Inhibitor from Human Plasma Fraction IV-1 by Ion Exchange Chromatography," *Vox Sang*, 1998, 74:232-241.

Choay et al., "Structural studies on a biologically active hexasaccharide obtained from heparin," *Ann. NY Acad. Sci.*, 1981, 370:644-649.

Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.

Colman, "Production of therapeutic proteins in the milk of transgenic livestock," *Biochem. Soc. Symp.*, 1998, 63:141-147.

Conradt et al., "Expression of Human Interleukin-2 in Recombinant Baby Hamster Kidney, Ltk, and Chinese Hamster Ovary Cells. Structure of O-linked carbohydrate chains and their location within the polypeptide," *J. Biol. Chem.*, 1989, 264(29):17368-17373.

Corey and Clark, "A new method for the synthesis of 2-pyridinethiol carboxylic ester," *Tetrahedron Lett.*, 1979, 31:2875-2878.

de Koning et al., "An approach to the synthesis of peptide-PNA-peptide conjugates via native ligation," *Tetrahedron Lett.*, 2002, 43(45): 8173-8176.

Denzlinger et al., "Differential Activation of the Endogenous Leukotriene Biosynthesis by Two Different Preparations of Granulocyte-Macrophage Colony-Stimulating Factor in Healthy Volunteers," *Blood*, 1993, 81(8):2007-2013.

Donahue et al., "Effects of N-linked Carbohydrates on the In Vivo Properties of Human GM-CSF," *Cold Spring Harbor Symp. Quant. Biol.*, 1986, 51:685-692.

Edmunds et al., "Transgenically Produced Human Antithrombin: Structural and Functional Comparison to Human Plasma-Derived Antithrombin," *Blood*, 1998, 91(12):4561-4571.

Ernst et al. (eds.), *Carbohydrates in Chemistry and Biology*, 2000, Part I, vol. 1-2, Whiley-VCH Weinheim (TOC only).

European Pharmacopoeia, 2001, 911-917.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271(5):907-919.

Franzen and Svensson, "Structural Studies on the Carbohydrate Portion of Human Antithrombin III," *J. Biol. Chem.*, 1980, 255(11):5090-5093.

Fujiki et al., "Studies on the disulfide bonds in human pituitary follicle-stimulating hormone," *Biochim. Biophys. Acta*, 1980, 624:428-435.

Goldstein and Gelb, "An alternate preparation of thioester resin linkers for solid-phase synthesis of peptide C-terminal thioacids," *Tetrahedron Lett.*, 2000, 41(16):2797-2800.

Goronzy et al., "T-Cell Derived Lymphokines as Regulators of Chronic Inflammation: Potential Targets for Immunomodulation?" *Am. J. Ther.*, 1996, 3(2):109-114.

Gribben et al., "Development of antibodies to unprotected glycosylation sites on recombinant GM-CSF," *Lancet*, 1990, 335:434-437.

Harris et al., "Pegylation. A novel process for modifying pharmacokinetics," *Clin. Pharmacokinet*, 2001, 40(7): 539-551.

He et al., "A simplified system for generating recombinant adenoviruses," *Proc. Natl. Acad. Sci USA*, 1998, 95:2509-2514.

Hodges and Chan, "Locations of Oligosaccharide Chains in Human α1-Protease Inhibitor and Oligosaccharide Structures at Each Site," *Biochemistry*, 1982, 21:2805-2810.

Hodges et al., "Structure of the Oligosaccharide Chains in Human α₁-Protease Inhibitor," *J. Biol. Chem.*, 1979, 254(17):8208-8212.

Hovgaard et al., "Clinical pharmacokinetic studies of a human haemopoietic growth factor, GM-CSF," *Eur. J. Clin. Inv.*, 1992, 22:45-49.

Hovinen et al., "Ethyl[2-deoxy-5-0-(4,4'-dimethoxytrityl)-α-and β-D-*erythro*-pentofuranosyl]acetates as versatile intermediates in nucleic acid chemistry," *Nucleosides Nucleotides*, 1999, 18:1263-1264.

Iakovenko et al., "Semi-synthetic Rab proteins as tools for studying intermolecular interactions," *FEBS Letters*, 2000, 468:155-158.

Ingenito et al., "Solid Phase Synthesis of Peptide C-Terminal Thioesters by Fmoc/*t*-Bu Chemistry," *J. Am. Chem. Soc.*, 1999, 121:11369-11374.

Jaques et al., "N.M.R. spectroscopy and calcium binding of sialic acids: N-glycolylneuraminic acid and periodate-oxidized N-acetylneuraminic acid," *Carb. Res.*, 1980, 83:21-32.

Karpusas et al., The crystal structure of human interferon β at 2.2-Å resolution, *Proc. Natl. Acad. Sci. USA*, 1997, 94:11813-11818.

Kaufman et al., "Synthesis, Processing, and Secretion of Recombinant Human Factor VIII Expressed in Mammalian Cells," *J. Biol. Chem.*, 1988, 263(13):6352-6362.

Kaushansky et al., "Role of Carbohydrate in the Function of Human Granulocyte-Macrophage Colony-Stimulating Factor," *Biochemistry*, 1987, 26:4861-4867.

Keene et al., "Expression of Biologically Active Human Follitropin in Chinese Hamster Ovary Cells," *J. Biol. Chem.*, 1989, 264(9):4769-4775.

Kochendoerfer et al., "Design and Chemical Synthesis of a Homogeneous Polymer-Modified Erythropoiesis Protein," *Science*, 2003, 299(5608):884-887.

Kraehenbuhl et al., "Preparation and characterization of an immuno-electron microscope tracer consisting of a heme-octapeptide coupled to Fab," *J. Exp. Med.*, 1974, 139:208-223.

Lahiri et al., "Antithrombin-Heparin Cofactor: An Inhibitor of Plasma Kallikrein," *Arch. Biochem. Biophys.*, 1976, 175:737-747.

Lapthorn et al., "Crystal structure of human chorionic gonadotropin," *Nature*, 1994, 369:455-461.

Levy et al., "Recombinant Antithrombin: Production and Role in Cardiovascular Disorder," *Sem. Thromb. Hem.*, 2001, 27(4):405-416.

Li et al., "Direct preparation of peptide thioesters using an Fmoc solid-phase method," *Tetrahedron Lett.*, 1998, 39(47):8669-8672.

Lin et al., "$_L$-Cysteine as a water-soluble cation scavenger in the removal of the 2,4,6-trimethoxybenzyl group from thiols," *Tetrahedron Lett.*, 2002, 43:4531-4533.

March, "Delocalized Chemical Bonding," *Adv. Org. Chem.*, 1992, 4th Edition, John Wiley and Sons, New York, Chapter 2 pp. 26-292.

Masamune et al., "A General, Selective 3695 Synthesis of Thiol Esters," *Can. J. Chem.*, 1975, 53:3693-3595.

Masamune et al., "Tylonolide Hemiacetal, the Aglycone of Tylosin, and Its Partial Synthesis," *J. Am. Chem. Soc.*, 1976, 98:7874-7875.

Masuda et al., "Synthesis and Anti-Influenza Evaluation of Orally Active Bicyclic Ether Derivatives Related to Zanamivir," *Bioorganic & Medicinal Chemistry Letters*, 2003, 13:669-673.

Mega et al., "Studies on the Oligosaccharide Chains of Human α₁-Protease Inhibitor. I. Isolation of glycopeptides," *J. Biol. Chem.*, 1980, 255(9):4053-4056.

Mega et al., "Studies on the Oligosaccharide Chains of Human α₁-Protease Inhibitor. II. Structure of oligosaccharides," *J. Biol. Chem.*, 1980, 255(9):4057-4061.

Menache, "Antithrombin III: Introduction," *Semin. Hematol.*, 1991, 28:1-2.

Menache et al., "Antithrombin III: physiology, deficiency, and replacement therapy," *Transfusion*, 1992, 32:580-588.

Ming et al., "Interleukin 6 is the Principal Cytolytic T Lymphocyte Differentiation Factor for Thymocytes in Human Leukocyte Conditioned Medium," *J. Mol. Cell. Immunol.*, 1989, 4:203-212.

Moonen et al., "Increased biological activity of deglycosylated recombinant human granulocyte/macrophage colony-stimulating factor produced by yeast or animal cells," *Proc. Natl. Acad. Sci. USA*, 1987, 84:4428-4431.

Mori et.al., "The Activation of Type 1 and Type 2 Plasminogen by Type I and Type II Tissue Plasminogen Activator," *J. Biol. Chem.*, 1995, 270(7):3261-3267.

Muir et al., "Expressed protein ligation: A general method for protein engineering," *Proc. Natl. Acad. Sci. USA*, 1998, 95:6705-6710.

Mukaiyama et al., "Peptide Synthesis *via* Oxidation-Reduction Condensation by the Use of Non-metallic Compound as a Mercaptan Scavenger," *Bull. Chem. Soc. Jpn.*, 1970, 43:1271.

Mumberg et al., "Regulatable promoters of *Saccharomyces cerevisiae*: comparison of transcriptional activity and their use for heterologous expression," *Nucl. Acids Res.*, 1994, 22(25):5767-5768.

Murano et al., "Some properties of antithrombin-III and its concentration in human plasma," *Thromb. Res.*, 1980, 18:259-262.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and Characterization of Three Forms of Differently Glycosylated Recombinant Human Granulocyte-Macrophage Colony-Stimulating Factor," *Arch. Biochem. Biophys.*, 1991, 286(2):562-568.

Olson et al., "Role of the Antithrombin-binding Pentasaccharide in Heparin Acceleration of Antithrombin-Proteinase Reactions. Resolution of the antithrombin conformational change contribution to heparin rate enhancement," *J. Biol. Chem.*, 1992, 267(18):12528-12538.

Olson and Björk, "Predominant Contribution of Surface Approximation to the Mechanism of Heparin Acceleration of the Antithrombin-Thrombin Reaction. Elucidation from salt concentration effects," *J. Biol. Chem.*, 1991, 266(10):6353-6364.

Opal et al., "Antithrombin, heparin, and heparan sulfate," *Crit. Care Med.*, 2002, 30(5):S325-S331.

Pelter et al., "Synthesis of Thioesters by Reactions of Carboxylic Acids with Tris-(ethylthio)borane," *J. Am. Chem. Soc., Perkin Trans I*, 1977, 1672-674.

Peterson, *The Physiological Inhibitions of Blood Coagulation and Fibrinolysis*, 1979, Elsevier/ North-Holland Biomedical Press, p. 43.

Pike et al., "Heparin-dependent Modification of the Reactive Center Arginine of Antithrombin and Consequent Increase in Heparin Binding Affinity," *J. Biol. Chem.*, 1997, 272 32:19652-19655.

Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," *Blood*, 1994, 84(12):4078-4087.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys®) for the treatment of hepatitis C," *Advanced Drug Delivery Reviews*, 2002, 54:571-586.

Reischl (ed)., *Molecular Diagnosis of Infectious Diseases*, 1997, vol. 13, Totowa NJ, Humana Press Inc. (TOC Only).

Reidhaar-Olson et al., "Identification of Residues Critical to the Activity of Human Granulocyte Colony-Stimulating Factor," *Biochemistry*, 1996, 35:9034-9041.

Revoltella et al., "Natural and Therapy-Induced Anti-GM-CSF and Anti-G-CSF Antibodies in Human Serum," *Leukemia and Lymphoma*, 1997, 26:29-34.

Roemisch et al., "Antithrombin: a new look at the actions of a serine protease inhibitor," *Blood Coagul. Fibrinolysis*, 2002, 13:657-670.

Rosenberg, "Role of heparin and heparinlike molecules in thrombosis and atherosclerosis," *Fed. Proc.*, 1985, 44:404-409.

Rosenberg et al., "Antithrombin-III," *Rev. Hematol.*, 1986, 2:351-416.

Schlesinger, "Alphaviruses—vectors for the expression of heterologous genes," *Trends Biotech.*, 1993, 11:18-22.

Schröter et al., "Male-specific Modification 29873 of Human CD52," *J. Biol. Chem.*, 1999, 274(42):29862-29873.

Shin et al., "Fmoc-Based Synthesis of Peptide-$^\alpha$Thioesters: Application to the Total Chemical Synthesis of a Glycoprotein by Native Chemical Ligation," *J. Am. Chem. Soc.*, 1999, 121:11684-11689.

Spellman et al., "Carbohydrate Structures of Human Tissue Plasminogen Activator Expressed in Chinese Hamster Ovary Cells," *J. Biol. Chem.*, 1989, 264(24):14100-14111.

Stetsenko and Gait, Efficient Conjugation of Peptides to Oligonucleotides by "Native Ligation," *J. Org. Chem.*, 2000, 65:4900-4908.

Stewart et al., "Identification of the Mechanism Responsible for the Increased Fibrin Specificity of TNK-Tissue Plasminogen Activator Relative to Tissue Plasminogen Activator," *J. Biol. Chem.*, 2000, 275(14):10112-10120.

Tam et al., "Peptide Synthesis Using Unprotected Peptides Through Orthogonal Coupling Methods," *Proc. Natl. Acad. Sci. USA*, 1995, 92:12485-12489.

Tebbutt, "Technology evaluation: transgenic α-1-antitrypsin (AAT), PPL Therapeutics," *Curr. Opin. Mol. Ther.*, 2000, 2(2):199-204.

Thim et al., "Amino Acid Sequence and Posttranslational Modification of Human Factor VII$_a$ from Plasma and Transfected Baby Hamster Kidney Cells," *Biochemistry*, 1988, 27:7785-7793.

Toole et al., "Molecular cloning of a cDNA encoding human antihaemophilic factor," *Nature*, 1984, 312:342-347.

Travis and Salvesen, "Human plasma proteinase inhibitors," *Ann. Rev. Biochem.*, 1983, 52:655-709.

Veronese et al., "Peptide and Protein PEGylation—A Review of Problems and Solutions," *Biomaterials*, 2001, 22(5):405-417.

Wadhwa et al., "Immunogenicity of Granulocyte-Macrophage Colony-Stimulating Factor (GM-CSF) Products in Patients Undergoing Combination Therapy with GM-CSF," *Clin. Cancer Res.*, 1999, 5:1351-1361.

Watanabe et al., "A facile synthesis of carboxylic thiol esters from carboxylic acids and thiols," *Chem. Lett.*, 1976, 741-742.

Weisshaar et al., "NMR investigations of the N-linked oligosaccharides at individual glycosylation sites of human lutropin," *Eur. J. Biochem.*, 1991, 195:257-268.

Wright et al., "High level expression of active human alpha-1-antitrypsin in the milk of transgenic sheep," *Biotechnology*, 1991, 9:830-834.

Yoshitake et al., "Nucleotide Sequence of the Gene for Human Factor IX (Antihemophilic factor B)," *Biochemistry*, 1985, 24:3736-3750.

Cera et al., "Water-soluble polysaccharide-anthracycline conjugates: Biological Activity," *Anti-Cancer Drug Design*, 1992, 7(2):143-151.

Dieterich et al, "Hydroxyethyl starch antibodies in humans: Incidence and clinical relevance," *Anesth. Analg,*, 1998, 86:1123-1126.

Gaucher et al., "Stereospecific synthesis and characterization of aminoglycoside ligands from diethylenetriamine," *J. Organic Chem.*, 1999, 64:4012-4015.

Guillaumie et al., "Immobilization of pectin fragments on solid supports: Novel coupling by thiazolidine formation," *Bioconjugate Chem.*, 2002, 13:285-294.

Liu et al., "Characterization of the structural and functional changes of hemoglobin in dimethyl sulfoxide by spectroscopic techniques," *Biochim. Biophys. Acta*, 1998, 138:53-60.

Merck Index 2006, Definition of Dimethyl Sulfoxide, Merck & Co., 14th Edition, accessed online: http//themerckindex.cambridgesoft.com/themerckindex/index/.asp on Sep. 4, 2007.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Radomsky and Temeriusz, "Thiazolidine-4(R)-carboxylic acids derived from sugars: part I, C-2-epimerisation in aqueous solutions," *Carb. Res.*, 1989, 187:223-237.

Shao and Tam, "Unprotected peptides as building blocks for the synthesis of peptide dendrimers with oxime, hydrazone and thiazolidine linkages," *J. Am. Chem. Soc.*, 1995, 117(14):3893-3899.

Yang et al., "Functional changes of carboxymethyl potato starch by conjugation with amino acids," *Biosci. Biotechnol. Biochem.*, 1995, 59(12):2203-2206.

Anderson and Meister, "Inhibition of γ-glutamyl transpeptidase and induction of glutathionuria by γ-glutamyl amino acids," *Proc. Natl. Acad. Sci. USA*, 1986, 83:5029-5032.

Axén et al., "Chemical Coupling of Peptides and Proteins to Polysaccharides by Means of Cyanogen Halides," *Nature*, 1967, 214:1302-1304.

Cervigni et al., "Synthesis of Glycopeptides and Lipopeptides by Chemoselective Ligation," *Angewandte Chemie International Edition in English*, 1996, 35(11):1230-1232.

Chaplin and Kennedy (eds.), Carbohydrate Analysis: a practical approach, 1994, 2nd Edition, Chapter 1 "Monosaccharides" pp. 1-41, Chapter 2 "Oligosaccharides" pp. 42-72, Chapter 3 "Neutral Polysaccharides" pp. 73-124, Chapter 5 "Glycoproteins" pp. 175-177 and 181-293, IRL Press.

*Dictionary of Chemistry and Chemical Technology*, 2003, p. 769 (English translation provided).

Lee et al., "Conjugation of Trypsin by Temperature-Sensitive Polymers Containing a Carbohydrate Moiety: Thermal Modulation of Enzyme Activity," *Biotechnol. Prog.*, 1998, 14:508-516.

Luo et al., "Controlled DNA delivery systems," *Pharm. Res.*, 1999, 16(8):1300-1308.

*Römpp Chemielexikon*, Thieme Verlag Stuttgart, Germany, 9th edition, 1990, vol. 9, pp. 2281-2285.

Somogyi, "Determination of reducing sugars," *Meth. Carb. Chem.*, 1962, 1:384-386.

Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-19568.

Wasley et al., "The Importance of N- and O-Linked Oligosaccharides for the Biosynthesis and In Vitro and In Vivo Biologic Activities of Erythropoietin," *Blood*, 1991, 77(12):2624-2632.

Bayer et al., "The Avidin-Biotin Complex in Affinity Cytochemistry," *Meth. Enzymol.*, 1979, 62:308-315.

Heitzmann and Richards, "Use of the Avidin-Biotin Complex for Specific Staining of Biological Membranes in Electron Microscopy," *Proc. Natl. Acad. Sci. USA*, 1974, 71(9):3537-3561.

Organikum, Organisch-chemisches Grundpraktikum, 1984, VEB Deutscher Verlag der Wissenschaften, p. 472 (with English translation and verification).

Tam et al., "Peptide Synthesis Using Unprotected Peptides Through Orthogonal Coupling Methods," *Proc. Natl. Acad. Sci. USA*, 1995, 92:12485-12489.

Pierce Chemical Technical Library, "cross-linking," 1994, 45 pages.

Carey and Sundberg, "Organische Chemie," VCH Verlagsgesellschaft mbH, Weinheim (DE), 1995, pp. 432-433 and 455 (English translation provided).

Peri et al., "Chemo- and Stereoselective Glycosylation of Hydroxylamino Derivatives: A Versatile Approach to Glycoconjugates," *Tetrahedron*, 1998, 54:12269-12278.

Heindel et al., "Hydrazide Pharmaceuticals as Conjugates to Polyaldehyde Dextran: Syntheses, Characterization, and Stability," *Bioconj. Chem.*, 1990, 1:77-82.

Wilchek and Bayer, "Labeling Glycoconjugates with Hydrazide Reagents," *Meth. Enzymol.*, 1987, 138:429-442.

Anno et al., "Sugar Chemistry," 1995, p. 31 (English translation provided).

Lund et al., "Assessment of methods for covalent binding of nucleic acids to magnetic beads, Dynabeads™, and the characteristics of the bound nucleic acids in hybridization reactions," *Nucl. Acids Res.*, 1988, 16(22):10861-10880.

Wang et al., "Delivery of Antisense Oligonucleotides Using HPMA Polymer: Synthesis of A Thiol Polymer and Its Conjugation to Water-Soluble Molecules," *Bioconj. Chem.*, 1998, 9:749-757.

\* cited by examiner

Fig. 1: GPC chromatogram of coupling III ox-HES 130 kD to HSA

Fig. 2: GPC chromatogram of coupling IV ox-HES 130 kD to HSA

Fig. 3: GPC chromatogram of coupling V ox-HES 130 kD to HSA (reaction time 2 hours)

Fig. 4: GPC chromatogram of coupling V ox-HES 130 kD to HSA (after complete reaction)

Fig. 5a: GPC analysis of the reaction kinetics of coupling V ox-HES 10 kD to HSA after 2 hours Fig. 5b: GPC analysis of the reaction kinetics of coupling V ox-HES 10 kD to HSA after 16 hours Fig. 6: GPC analysis of the reaction mixture after 24 hours incubation of coupling VII ox-HES 130 kD to HSA Fig. 7: GPC chromatogram of coupling V HES 130 kD to HSA and hydroboron reduction

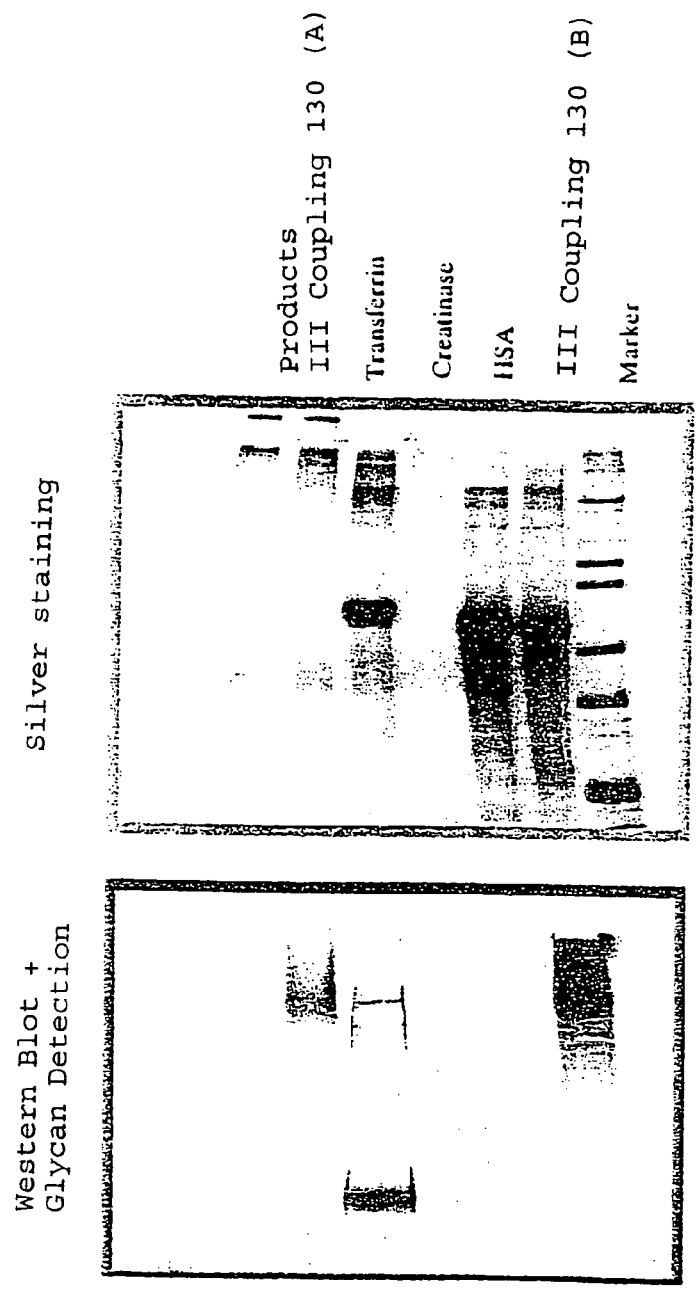

Fig. 8: Top Picture: SDS PAGE of the coupling reactions III (Processes A and B) between HSA and oxHES 130 kD and HES 130 kD, respectively, with silver staining (Lane 1: Coupling III Process A); Lane 2: Transferrin; Lane 3 Creatinase; Lane 4: non-modified HSA; Lane 5: Coupling III (Process B); Lane 6: Marker Bottom picture: Western Blot with Glycan detection of the same samples, Transferrin (Lane 2) functioning as positive control and Creatinase (Lane 3) and HSA (Lane 4) as negative control Fig. 9: SDS-PAGE, silver stained 12 % PAA (top) and Western Blot/Glycan (bottom) of the reaction mixture from coupling V ox-HES 10 kD with HAS

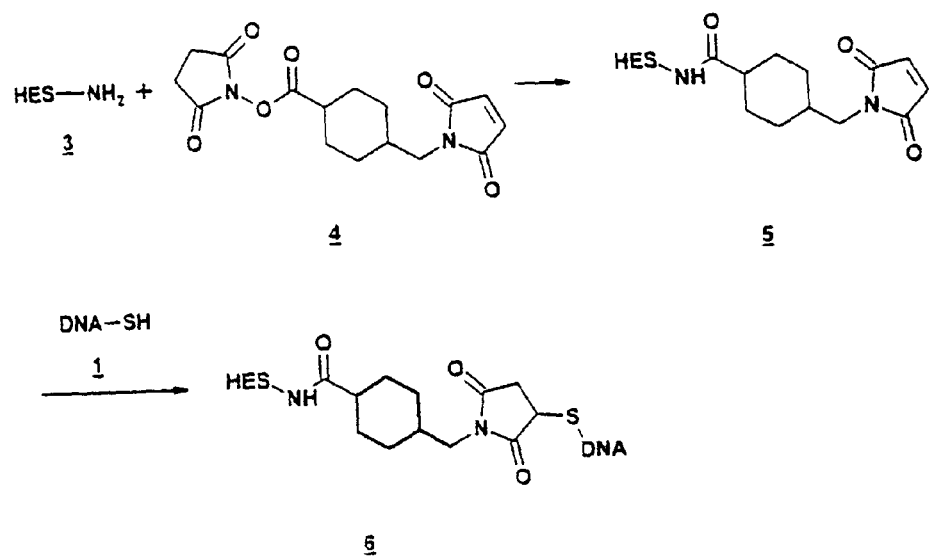
Structure of thio-modification of the DNA
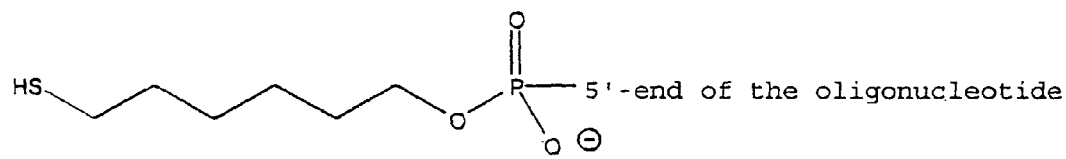
Structure of SMCC
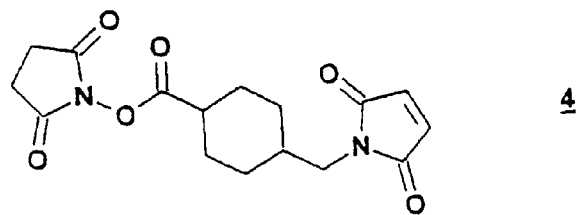
Fig. 10

CONJUGATES OF HYDROXYALKYL STARCH AND AN ACTIVE AGENT

CROSS-REFERENCE TO RELATED APPLICATIONS

This application is a national phase application under 35 U.S.C. §371 of International Application Number PCT/EP02/02928, filed Mar. 15, 2002, the disclosure of which is hereby incorporated by reference in its entirety, and which claims the benefit of German Patent Application Number 101 12 825.8, filed Mar. 16, 2001.

INCORPORATION OF SEQUENCE LISTING

A paper copy of the Sequence Listing and a computer readable form of the sequence listing on diskette, containing the file named 18970.002SEQLIST.txt, which is 801 bytes in size (measured in MS-DOS), and which was created on Sep. 16, 2003, are herein incorporated by reference.

The present invention relates to compounds comprising a conjugate of hydroxyalkyl starch (HAS) and an active ingredient, wherein the hydroxyalkyl starch is coupled to the active ingredient either directly or via a linker. The invention further relates to processes for the preparation of a covalent HAS-active ingredient conjugate in which HAS and an active ingredient are reacted with each other in a reaction medium, wherein the reaction medium is water or a mixture of water with an organic solvent, having at least 10 weight-% water. The invention further relates to the medical use of the conjugates.

TECHNICAL BACKGROUND

The clinical use of many active ingredients of pharmaceuticals is adversely affected by a number of problems (e.g. Delgado et al., Critical Reviews in Therapeutic Drug Carrier Systems, Vol. 9 (3, 4), (1992) pp. 249-304). Parenterally administered native proteins are subject for example to excretion by the reticuloendothelial system, the liver, the kidney and the spleen. Excretion depends on the charge of carbohydrate chains, the presence of cellular receptors for the protein and molecule shape and size. The excretion limit of the glomerular filtration of the kidney is for example approx. 67 kD.

As a result of proteolytic degradation, a rapid loss of biological activity can also be observed.

Proteins expressed by bacteria as well as other recombinant proteins can have an increased immunogenicity and provoke life-threatening hypersensitivity reactions. Corresponding reactions naturally prevent the medical use of these products.

For this reason, research has been carried out systematically in the state of the art already since the end of the 70s on the improvement of the properties of exogenic proteins by chemical modification, in particular polymerization or coupling to macromolecular polymers. Many projects concentrated on the preparation of conjugates from proteins or other active ingredients on the one hand and polyethylene glycol (PEG) on the other (e.g. U.S. Pat. No. 4,179,337). The advantages expected from respective coupling reactions comprise improved in vivo half-life of the proteins, reduced toxicity, improved stability and improved solubility of the active ingredients (Abuchowski and Davis, Enzymes as drugs, Holcenberg and Rubberts, Publisher, pp. 367-383, John Wiley & Sons N.Y. (1981)).

The process of coupling the active ingredients proved to be problematic however, as the active group of the protein was inactivated by coupling to PEG or the reactions did not provide the reaction product in a suitable yield. To achieve a specific coupling which does not adversely affect the activity of the active ingredient, active groups were introduced into PEG or the active ingredient or the compounds were coupled with a linker. For this purpose, PEG is normally provided with an active group which is subsequently covalently bound to a group of a protein capable of being coupled.

Thus for example, the loss of the binding activity of antibodies and their fragments after their coupling to PEG was described (Kitamura et al., Cancer Res., Vol. 51 (1991), pp. 4310-4315; and Pedley, et al., Br. J. Cancer, Vol. 79 (1994), pp. 1126-1130). To solve this problem, Chapman et al. (Nature Biotech., Vol. 17 (1999), pp. 780-783) suggest binding PEG to certain binding regions of the antibody.

The loss of activity of the coupling partner is also described in WO 95/13090. As a solution, it is suggested to activate PEG with a reactive group and to bind PEG to α-interferon in the presence of a surfactant via this reactive group. Cited as preferred reactive group is N-succinimide carbonate, which is said to form a urethane bond with the ε-amino group of lysine under the conditions named.

WO 96/41813 also discloses processes for the preparation of a polymer-polypeptide conjugate in which the polymer (in particular PEG) is derivatised at a specific region and then bound to a polypeptide. An amino-oxi-acetyl group is preferably introduced into PEG and this compound is then bound to a polypeptide, in particular to IL-8, hG-CSF and IL-1.

In the literature, there are thus numerous examples of corresponding conjugates; e.g. PEG-insulin conjugates in U.S. Pat. No. 4,179,337, PEG-bovine-haemoglobin conjugates in U.S. Pat. No. 4,412,989, PEG-ribonuclease conjugates and PEG superoxide dismutase conjugates in Veronese et al. Applied Biochem. Biotech., Vol. 11, 141-152 (1995), PEG-IL-2 conjugates or PEG-IFN-β conjugates in U.S. Pat. No. 4,766,106, PEG-polymyxin conjugates in WO 90/15628 and PEG-IL-2 conjugates in WO 90/07939. Some conjugates are now in clinical application. For example, the properties of the enzyme asparaginase were improved by conjugate formation with PEG, and a PEG-asparaginase conjugate is commercially available under the trademark Oncaspar® for cancer therapy. Recently, a PEG-coupled G-CSF was approved by the US Food and Drug Administration (Pegfilgastim). A large number of further pegylated products are in different phases of clinical development, for example PEG-CDP870, PEG-Dronabinol, etc. (e.g. PEG-pipeline at www.enzon.com or www.inhale.com).

Not only proteins, but other compounds were also coupled to PEG and other polymers according to this scheme. WO 97/33552 and WO 97/38727 disclose for example the coupling of paclitaxel to PEG and the use of the conjugate for the treatment of tumors. The use of a PEG-camptothecin conjugate for the treatment of tumors is being studied by Enzon in phase I clinical trials.

Antibiotics have also been coupled to PEG. Dowling and Russell, for example, describe the pharmacokinetics of an oxytetracyclin-PEG conjugate (J. Vet. Pharmacol. Ther., vol. 23 (2000), 107-110). In the state of the art, antibiotics have also been derivatized using other methods in order to obtain new functions. For example, a depot penicillin was produced, which is a procain-penicillin derivative, i.e. a salt of the penicillin with the procain base. This derivative has an extended activity and it is used, for example, in the therapy of Syphilis.

Coupling reactions with more than two compounds have also been demonstrated. For example, WO 93/23062 discloses the preparation of a coupling product from an antibody directed against a B cell lymphoma, activated PEG and a toxin.

PEG-active ingredient conjugates however do not have a natural structure for which in vivo decomposition pathways have been described. Amongst others for this reason, in addition to the PEG conjugates, other conjugates and protein polymers have been produced for solving the above-named problems. Thus, there are a number of processes for cross-linking different proteins and binding of proteins to macro-molecules (e.g. summary in Wong, S. S., "Chemistry of protein conjugation and cross linking", CRCS, Inc. (1993)).

Hydroxyethyl starch (HES) is a derivative of a naturally occurring amylopectin and is broken down in the body by α-amylase. The preparation of HES-protein conjugates has already been described in the state of the art (e.g. HES-haemoglobin conjugates in DE 26 16 086, hereby incorporated by reference, or DE 26 46 854, hereby incorporated by reference).

Haemoglobin is a protein which could be of great clinical importance as a blood-replacement and oxygen-carrier agent (so-called Haemoglobin-Based-Oxygen Carrier, HBOC). However, although the demand for such a product was recognized early on (e.g. Rabiner, J. Exp. Med. 126, (1967) 1127), none of the known HBOC products has as yet achieved the status of an approved drug.

The natural haemoglobin consists of two α and β peptide chains which each bind a haeme as a prosthetic group. Isolated haemoglobin molecules are however very unstable and rapidly break down into the more stable α,β dimers (MW 32 kDa). The biological half-life of isolated haemoglobin in the blood circulation is approx. 1 hour, as the dimers are rapidly eliminated via the kidneys. In this process, the dimers produce nephrotoxic side effects (e.g. Bunn & Jandl, J. Exp. Med. 129, (1967) 925-934). Development work on derivatized haemoglobin molecules was therefore primarily directed towards the intramolecular cross-linking of haemoglobin, the intermolecular cross-linking to form polymeric HBOC forms and/or the coupling to polymers.

The known haemoglobin conjugates are described for example in Xue and Wong (Meth. in Enzymol., 231 (1994), pp. 308-322, hereby incorporated by reference) and in DE 26 16 086 and DE 26 46 854, hereby incorporated by reference. The latter discloses processes by means of which haemoglobin is bound to HES by firstly reacting HES with sodium periodate. Dialdehydes form, to which haemoglobin is bound. On the other hand, DE 26 16 086, hereby incorporated by reference, describes the coupling of haemoglobin to HES according to a process in which firstly a cross-linking agent (e.g. Bromcyan) is bound to HES and haemoglobin is then bound to the intermediate product.

HES is a substituted derivative of the carbohydrate polymer amylopectin which occurs in maize starch in a concentration of up to 95%. HES has advantageous rheological properties and currently used in the clinic as a volume-replacement agent and for haemodilution therapy (Sommermeyer et al., Krankenhauspharmazie, Vol. 8(8), (1987), pp. 271-278; and Weidler et al., Arzneim.-Forschung/Drug Res., 41, (1991) 494-498).

Amylopectin consists of glucose units, wherein the main chains have α-1,4-glycosidic bonds, but α-1,6-glycosidic bonds are present at the branching sites. The physical-chemical properties of this molecule are determined essentially by the type of glycosidic bonds. Because of the branched α-1,4-glycosidic bond, helical structures form with approx. 6 glucose monomers per turn.

The physico-chemical and the biochemical properties of the polymer can be modified by substitution. The introduction of a hydroxyethyl group can be achieved by alkaline hydroxyethylation. The different reactivity of the relevant hydroxyl group in the unsubstituted glucose monomer vis-à-vis the hydroxyethylation can be exploited through the reaction conditions, a limited influence on the substitution pattern is thus possible.

HES is therefore essentially characterized via a molecular weight distribution and a degree of substitution. The degree of substitution can be described as DS "degree of substitution" which refers to the proportion of the substituted glucose monomers of all glucose units, or as MS ("molar substitution"), which gives the number of hydroxyethyl groups per glucose unit.

HES solutions are present as polydisperse compositions in which the individual molecules differ from each other with regard to the degree of polymerization, the number and arrangement of the branching sites, as well as their substitution pattern. HES is thus a mixture of compounds with different molecular weights. Accordingly, a specific HES solution is determined by an average molecular weight using statistical variables. $M_n$ is calculated as a simple arithmetic average in relation to the number of molecules (numerical average), whilst $M_w$, the weight average, represents the mass-related measurement variable.

A selective chemical binding of proteins to HES was however hitherto prevented by the fact that the HES is not activated selectively. Thus, the protein-HES conjugates known in the state of the art result from a non-selective coupling of Bromcyan-activated HES to haemoglobin (e.g. DE 26 16 086, hereby incorporated by reference). Corresponding processes can lead to polydisperse products with non-uniform properties and potentially toxic side effects.

A process was first disclosed by Hashimoto (Hashimoto et al., Kunststoffe, Kautschuk, Fasern, Vol. 9, (1992) pp. 1271-1279, hereby incorporated by reference) wherein the reducing aldehyde end group of a saccharide is selectively oxidized and a reactive ester (lactone) is obtained.

On the basis of this process, WO 98/01158 discloses that haemoglobin-hydroxyethyl starch conjugates can be obtained in which haemoglobin and HES are selectively linked to each other via amide bonds between free amino groups of the haemoglobin and the reducing end group of the HES present in oxidized form. Both the processes described in Hashimoto et al. and the processes according to WO 98/01158, hereby incorporated by reference, are however based on a reaction between saccharide (HES) and protein (haemoglobin) in organic solvent. Dimethyl sulfoxide (DMSO) was in fact used in the publication.

One of ordinary skill in the art is aware of the fact that many proteins are subject of a change in structure in organic solvents which is not reversed in aqueous solution. Regularly, a loss of activity occurs with the change in structure. In every case, a costly removal of the organic solvent is necessary, as even residual proportions of organic solvents may not be acceptable for the intended medical use. Even the potential danger of impurities and changes in structure of the proteins is to be excluded with regard to the intended use.

The object of the present invention is thus to provide improved hydroxyalkyl starch-active ingredient conjugates and processes for their preparation which lead to biologically active conjugates which can be used in everyday clinical practice. A further object of the present invention is to provide a process for the preparation of hydroxyalkyl starch-active ingredient conjugates wherein by-products are not produced in significant quantities, as these by-products also adversely affect the subsequent purification of the product to a significant extent.

This object was now surprisingly solved by compounds comprising a conjugate of hydroxyalkyl starch and an active ingredient, wherein the hydroxyalkyl starch is covalently bound to the active ingredient either directly or via a linker. Corresponding HAS-active ingredient conjugates are for example obtainable by processes, wherein HAS and an active ingredient are coupled in a reaction medium, wherein the reaction medium is water or a mixture of water with an organic solvent, which comprises at least 10 weight-% water.

The invention further relates to processes for the preparation of a covalent HAS-active ingredient conjugate, wherein HAS and at least one active ingredient are coupled in an aqueous reaction medium and is characterized in that the reaction medium is water or a mixture of water with an organic solvent, which comprises at least 10 weight-% water.

HAS is preferably oxidized before binding to the active ingredient, a specific oxidation of the reducing end groups being particularly preferred. Alternatively, the coupling can take place via the formation of a Schiff's base between HAS and an amine group-carrying active ingredient as intermediate product. This intermediate product is then reduced, resulting in the formation of a methylene amine group.

BRIEF DESCRIPTION OF THE FIGURES

FIG. 10 reaction scheme for the preparation of a HES-DNA conjugate;

Figure 1:
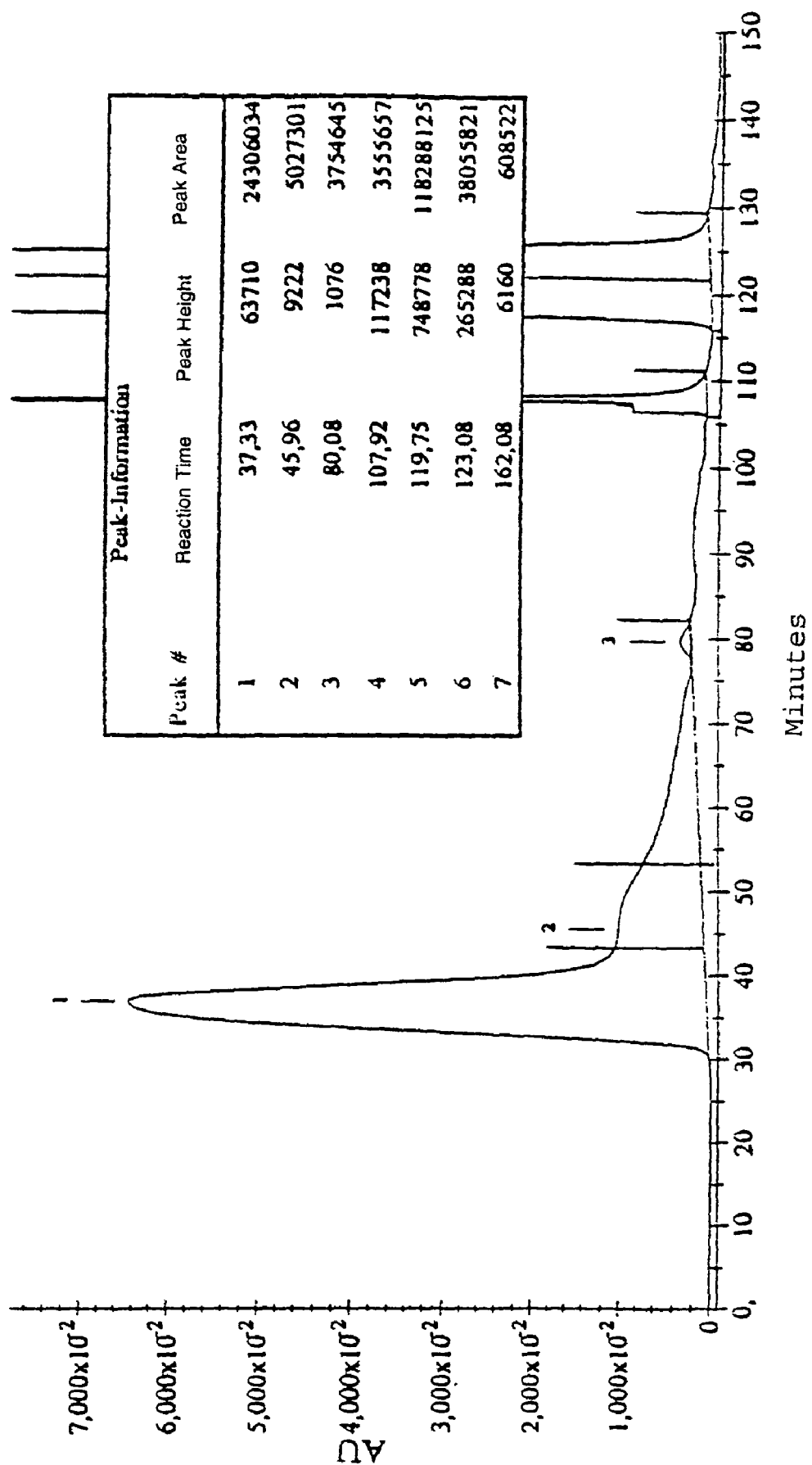
FIG. 1 GPC chromatogram of the coupling reaction between ox-HES 130 kD and HSA according to process A.III.

The present invention provides for the first time compounds comprising a conjugate of hydroxyalkyl starch and an active ingredient, wherein the hydroxyalkyl starch is covalently bound to the active ingredient either directly or via a linker. The present invention further provides HAS-active ingredient conjugates which can be prepared by processes, wherein HAS and at least one active ingredient are reacted with each other in an aqueous reaction medium. The processes are further characterized in that the reaction medium is water or a mixture of water with an organic solvent, which comprises at least 10 weight-% water.

Within the context of the present invention, a chemical compound is referred to as an active ingredient if the compound is suitable to be an active component of any composition for therapeutic or diagnostic purposes. Preferably, the active ingredient is an active component of a drug, i.e. the compound in a drug formulation which achieves a physiological effect after administration to a subject.

An overview of the approved drugs and their active ingredients is given in the pharmacopeia. All the active ingredients named in the pharmacopeia can be used for the preparation of the HAS-active ingredient conjugates by the process according to the invention. However, according to the present invention, the term active ingredient also comprises all compounds which, although known to be suitable for diagnostic or therapeutic use, were however not able to be used up to now for this purpose, because of the problems described above. The active ingredient is preferably a vitamin, vaccine, toxin, antibiotic (or antiinfective), antiarrhythmic, appetite suppressant, anesthetic, analgesic, antirheumatic, antiallergic, antiasthmatic, antidepressant, antidiabetic, antihistamine, antihypertonic or an antineoplastic agent. Structurally, it can be for example a hormone, steroid, lipid, protein, oligo- or polypeptide, a nucleic acid, in particular a D- or L-nucleic acid, such as a D-DNA, L-DNA, D-RNA or L-RNA. The use of proteins, peptides, D- or L-nucleic acids as HAS coupling partners is particularly preferred.

The compounds prepared according to the present invention retain the activity of the active ingredient and the advantageous properties of the HAS. As further advantages, the conjugates prepared according to the process according to the invention have an improved in vivo half-life of the active ingredients, reduced toxicity, improved stability and/or improved solubility of the active ingredients.

After administration, the HAS chain is shortened by the α-amylase in the plasma. Thus, the activity of the coupling product can be determined as activity of the native coupling product, i.e. directly after the coupling, or as activity of the metabolized coupling product, i.e. after in vivo metabolizing of the coupling product. In vivo metabolizing can be simulated by an in vitro degradation.

The activity of the active ingredient may be determined by methods which are known for this compound in the state of the art. For example, the activity of an antineoplastic agent is determined as inhibitory concentration (IC), and the activity of an antiinfective agent is determined as minimal inhibitory concentration (MIC). Preferably, the determination is performed in vitro with appropriate target cells (e.g. Chow et al., Haematologica, Volume 86 (2001), pages 485-493, herein incorporated by reference). The in vitro effects can further be confirmed by a relevant animal model (e.g. for example the mouse model of the renal cell carcinoma described in Changnon et al., e.g. BJU Int., Volume 88 (2001), page 418-424, herein incorporated by reference).

Compared to the non-coupled substance, the native coupling product can have an increased or reduced activity. Preferably, however, the activity is not reduced more than 5-fold, more preferably not more than 3- or 2-fold. The metabolized product preferably has an activity comparable to that of the non-coupled substance, i.e. prior to the coupling, the metabolized conjugate has at least 50%, preferably at least 75% of the activity of the active ingredient, wherein a retention of at least 95% of the activity is particularly preferred.

In the context of the present invention, the term "hydroxyalkyl starch" is used to refer to starch derivatives which are substituted with a hydroxyalkyl group having 1 to 3 carbon atoms. Thus, the group designated as "hydroxyalkyl starch" comprises hydroxymethyl starch, hydroxyethyl starch and hydroxypropyl starch. The use of hydroxyethyl starch (HES) as a coupling partner is particularly preferred for all embodiments of the invention.

According to the invention, it is preferred that the hydroxyethyl starch has an average molecular weight (weight average) of 1-300 kDa, wherein an average molecular weight of 5 to 200 kDa is particularly preferred. Furthermore, hydroxyethyl starch may have a molar degree of substitution of 0.1 to 0.8 and a ratio of $C_2:C_6$-substitution in the range of 2-20, in each case relative to the hydroxyethyl groups.

For coupling the active ingredient to the HAS, it may be necessary in a first step to introduce an active group into the active ingredient and/or the HAS. Corresponding active groups can for example be thiol groups or amino groups (e.g. Examples).

Further, the active ingredient and the HAS can be coupled to each other by use of a linker. Any crosslinking agent can be used as a linker. Numerous crosslinking agents such as SMCC (succinimidyl-4-(N-maleimido-methyl)cyclohexane-1-carboxylate; e.g. Example 7) are commercially available and well-known to the person skilled in the art (e.g. alphabetic list of the "cross-linking reagents" in the product catalogue of the company Perbio and www.piercenet.com).

According to a further embodiment of the present invention, water-soluble antibiotic derivatives which contain an amino sugar, in particular HAS-daunorubicin and HAS-doxorubicin conjugates, and processes for their preparation, as far as they are disclosed in DE 101 29 369, herein incorporated by reference, are not within the scope of the present invention, e.g. DE 101 29 369 is disclosed with the proviso that said disclosure is not within the scope of the present invention.

According to a preferred embodiment, the present invention relates to compounds comprising a conjugate of HAS and an antineoplastic active ingredient and their use for the treatment of tumors.

Among others, tumor cells differ from normal somatic cells in that tumor cells are no longer subject to a physiological growth control and therefore have an increased rate of cell division. The therapeutic use of antineoplastic active ingredients in tumor therapy is based on this difference, since the toxic activity of the antineoplastic active ingredients is primarily directed against proliferating cells. As a consequence, compounds are designated as antineoplastic active ingredients or cytostatics if they exhibit a toxic activity against proliferating cells (basics of oncology and current therapeutic approaches are for example summarized in: Internistic Oncology, Schmoll et al. (eds.), Springer, 1996).

With respect to their chemistry, antineoplastic active ingredients represent a very heterogeneous group. In addition to the inhibition of proliferation, the induction of apoptosis, programmed cell death, gains importance in the discussions over the last years. A classification of the antineoplastic active ingredients can for example be performed based on the relevant target molecules (Schmoll et al., see above):

1. Compounds which inhibit DNA biosynthesis, for example as antimetabolites, such as MTX, 5-FU, Ara-C or hydroxy urea.
2. Compounds, which act on the DNA, for example by strand break induction, intercalation, modification of interstrand cross-linking, topoisomerase toxins, such as alkylating agents, platinum complexes, anthracyclins, bleomycin, actinomycin-D or epipodophyllo toxins.
3. Compounds which act on the RNA, for example by blocking mRNA-synthesis by intercalation or incorporation into the RNA, including anthracyclins, bleomycin, actinomycin-D or antimetabolites.
4. Compounds, which act on proteins, for example on the level of receptor binding (e.g. hormones or antagonists), by inhibition of tubulin polymerization (e.g. by vinca alkaloids), by protein cross-linking (for example by alkylating agents) or phosphorylation (e.g. by inhibitors of protein kinase C).

Due to the antineoplastic activity, all active ingredients have considerable side effects, which primarily occur as inhibition of fast proliferating tissues. For this reason, in particular erythro-, leuko- and trombopoiesis are inhibited and the growth of mucous membrane epithelia is adversely affected. As a consequence, gastrointestinal disorders or non-reversible impairments of spermatogenesis or anovulation, respectively, can occur. The skin and the skin accessory organs are also usually affected. For example, many patients suffer from a reversible loss of hair.

In severe cases, the side effects can lead to an acute loss of the kidney function and toxic-related organ damages to heart, lung, liver and nervous system. Finally, as a consequence of the immunosuppressive effect, an increased number of infections have to be expected.

The preparation and investigation of conjugates which contain an antineoplastic agent were therefore focused on the improvement of the tolerance of the active ingredient. For this purpose, different antineoplastic active ingredients have been coupled to macromolecules such as dextran (e.g. Kojima et al., J. Pharm. Pharmakol., Vol. 32 (1980), p. 30-34; Nakane et al., J. Pharm. Pharmakol., vol. 40 (1988), p. 1-6, Nomura et al., J. Controlled Release, Vol. 52 (1998), p. 239-252; Sato et al., J. Pharm. Sci., Vol. 78 (1989), p. 11-16, the disclosures of which are hereby incorporated by reference). In several cases, an improved anti-tumor effect of the conjugates was demonstrated.

As an alternative, active ingredients such as mitomycin C were also coupled to N-succinylchitosan (Song et al., J. Controlled Release, Vol. 42 (1996), p. 93-100; hereby incorporated by reference), carboxymethylchitin (Song et al., Arch. Pract. Pharm. Vol. 53 (1993), p. 141-147; hereby incorporated by reference) and oligopeptides (Soyez et al., J. Controlled Release, Vol. 47 (1997), p. 71-80; hereby incorporated by reference). When compared to the individual antineoplastic active ingredient, again, an improved anti-tumor activity of the conjugates was observed in the majority of analyses.

According to the invention it was now surprisingly found, that HAS-active ingredient conjugates which comprise an antineoplastic active ingredient have an improved toxic effect against tumor cells and/or a reduced toxicity for other cells. Therefore, the conjugates allow for a broader therapeutic range.

The plasma half-life of the conjugates is significantly increased. This allows conjugates to overcome the repair mechanisms in tumor cells by longer exposition. Simultaneously, the present invention enables slower flooding, in particular in healthy tissue, whereby a reduced peak concentration and an improved tolerance for the patient is achieved.

For the preparation of the conjugates according to the invention, any antineoplastic active ingredient can be used. The antineoplastic active ingredient can, for example, be selected from the group consisting of alkylating agents, antimetabolites, antibiotics or natural substances.

According to a preferred embodiment, the antineoplastic active ingredient is mitomycin C, cyclophosphamid, bleocin, chlorambucil, cisplatin, Ara-C, fludarabine, doxorubicin, etoposide, 5-FU, MTX, vinblastine, vincristine, vindesine, hydroxy urea, 6-MP or CCNU.

The use of mitomycin C as active ingredient is particularly preferred. Mitomycin C belongs to the group of antibiotics and contains an aziridine group and a quinone group and a mitosane ring. The active ingredient is used for the treatment of renal cell carcinoma and bladder tumors as well as other urologic diseases. The compound gains its activity only upon metabolization in hypoxyic cells (this means preferably in tumor cells) by intracellular enzymatic or spontaneous chemical reduction of the quinone and loss of the methoxy group. Preferably, HAS can be coupled to this methoxy group via a linker. After intracellularly cleaving off the substituent, the same active ingredient is present inside the cell which causes an alkylating cross-linking of the DNA thereby exhibiting its toxic effect. As an alternative, HAS may also be coupled to one of the two NH,—groups. Mitomycin C shows a typical tissue specificity. According to the invention, it is preferred that this specificity —in particular for excretory organs —is increased by HAS-coupling.

According to the invention, the antineoplastic active ingredient can be coupled to HAS by use of any method. However, a specific coupling to the reducing end groups of HAS is preferred, since this procedure generates a defined conjugate.

According to one embodiment of the invention, hydroxyethyl starch may be coupled to the methoxy group of mitomycin C. Coupling to the methoxy group of mitomycin C can take place via a linker.

According to a further embodiment, the present invention relates to processes for the preparation of a compound comprising a conjugate of HAS and an antineoplastic active ingredient. The process comprises steps, in which HAS is covalently coupled to an antineoplastic active ingredient, either directly or via a linker, and the conjugate is isolated.

Further, the invention relates to pharmaceutical compositions which comprise a compound comprising a conjugate of HAS and an antineoplastic active ingredient. The pharmaceutical composition can furthermore comprise a pharmaceutically compatible carrier and/or a cytokine. Preferably, the cytokine is IL-2, α-interferon, γ-interferon.

The pharmaceutical composition can be in any application form that is known in the state of the art. For example, the composition can be formulated for oral or parenteral administration. The formulation of the composition is performed according to processes known in the state of the art. In addition to the active ingredient, the composition generally comprises a pharmaceutically compatible carrier and one or more auxiliaries and optionally preservatives, solubility promoters, etc.

Finally, the present invention relates to the use of a compound comprising a conjugate of HAS and an antineoplastic active ingredient for the preparation of a medicament for the treatment of tumors and/or their metastases, in particular for the treatment of urologic tumors and/or metastases of urologic tumors, for the treatment of metastases of the renal cell carcinoma, or for the treatment of diseases of the lymphatic system, such as CLL, Hodgkin-lymphoma, NHL, multiple myeloma, Waldenström's syndrome. According to this embodiment of the invention, the medicament can further comprise a cytokine, such as IL-2, α-interferon, γ-interferon.

The use of the compounds according to the invention for the preparation of a medicament for the treatment of urologic tumors and/or metastases of urologic tumors, such as for the treatment of metastases of the renal cell carcinoma is particularly preferred. Presently, a curative therapy of the renal cell carcinoma can neither be achieved with a combination chemotherapy nor with mitomycin C alone. This might be due to the unfavourable pharmacokinetics of the compound, since the portion of renal elimination only amounts to approximately 18%. Since HAS is almost completely eliminated via the kidney, the conjugate exhibits a higher percentage of renal elimination compared to the non-conjugated substance. This embodiment of the present invention utilizes the intracellular intermediate storage of HAS. In particular, highly substituted HAS species (HAS 200/0.62) show an increased intracellular storage, in the extreme case even an overload. This phenomenon has also been observed in the area of the proximal tubule (Peron et al., Clinical Nephrology, Vol. 55 (2001), p. 408-411, hereby incorporated by reference).

According to this embodiment, the present invention provides an accumulation of an antineoplastic active ingredient in certain target cells or tissues. Therefore, the improved pharmacokinetics of the conjugates make it possible to achieve a considerably higher concentration in the cells of the target organ while using low systemic concentrations. This medical use is preferably employed on the hypernephroid carcinoma and the chromophylic renal carcinoma which constitute approximately 90% of all histological types.

According to an alternative embodiment, the invention relates to the use of the compounds according to the invention for the preparation of a medicament for the treatment of diseases of the lymphatic system, such as CLL, Hodgkin lymphoma, NHL, multiple myeloma, Waldenström's syndrome. By coupling of HAS to an antineoplastic active ingredient according to the invention, the intracellular uptake of the active ingredients is decelerated dependent on the chain length and the degree of substitution. Furthermore, radioactive kinetic studies have shown that HAS is stored in certain organs, among others in lymphatic organs, for a longer time than in the whole body (e.g. Bepperling et. al., Crit. Care, Vol. 3, Suppl. 1 (1999), p. 153, hereby incorporated by reference). Thus, accumulation of the conjugate in the target cells occurs which results in improved pharmacokinetics with a lower systemic toxicity.

The treatment of diseases of the lymphatic system using fludarabin as an active ingredient is preferred. Fludarabin is a halogenated adenine analogue which is resistant to deamination.

The invention further relates to the use of the compounds according to the invention for the preparation of a medicament for the treatment of cutaneous/local primary malignant neoplasms or their metastases. For this, two effects can be utilized, the directed increased uptake by the recited tissues and the decelerated transport of the HAS conjugates out of the tissue. Both effects lead to an accumulation of the conjugate in the target cells.

The invention further relates to the use of the compounds according to the invention for the preparation of a medicament for the treatment of diseases of the hematologic system or oncologic diseases, such as non-small cell lung cancer and small cell lung cancer, breast cancer, esophagus squamous cell carcinoma, renal cell carcinoma, testicular carcinoma, malignant melanoma, ALL or CML. In particular, when using the conjugates for the treatment of the renal cell carcinoma, advantages arise due to the strong accumulation of the compound in the affected tissue by the increased hydrophilicity of the conjugate and the stronger renal elimination resulting thereof. For this embodiment of the invention, the use of vindesine as active ingredient is particularly preferred.

The invention further relates to the use of the compound according to the invention for the preparation of a medicament, wherein the compound is used as a combination therapy with one or more further antineoplastic active ingredients or cytokines. The combination therapy can be performed by administration of an agent containing all active ingredients, or by administration of two or more different compositions, each of which containing one active ingredient.

The present invention further provides processes for the preparation of a medicament comprising a cytokine and a compound according to the invention which is suitable for new combination therapies. Corresponding agents are in particular suitable for the treatment of the advanced renal cell carcinoma.

According to another particularly preferred embodiment of the invention, conjugates of HAS and an antiarrhythmic active ingredient as well as their use for the treatment of arrhythmia are provided.

Deviations from the temporary sequence and regularity of the heartbeat (arrhythmia) from the normal heart rate are referred to as arrhythmia. In the majority of cases, these deviations are caused by cardiac excitation or conduction disorders. Substances which are suitable for the treatment of arrhythmia, in particular ventricular arrhythmia, are referred to as antiarrhythmic active ingredients or antiarrhythmics.

Dependent on the effect of the antiarrhythmic active ingredients it is distinguished between sodium channel blockers (quinidine, procainamide, disopyramide, etc.) beta-receptor blockers (atenolol, propanolol, etc.), selective repolarisation prolonging active ingredients (amiodarone, sotalol, etc.), calcium antagonists (verapamil, gallopamil, etc.) and local anesthetics.

However, the antiarrhythmic active ingredients customary in the state of the art partially exhibit a short duration of action. For example, adenosine is an antiarrhythmic active ingredient with a very short half-life. The duration of action of this substance is only several minutes. In many cases, prolongation of half-life and duration of action is necessary.

Additionally, several antiarrhythmic active ingredients have pro-arrhythmogenic side effects and partially even an increase in mortality.

The present invention provides, among others, improved antiarrhythmic active ingredients which, for example, have a prolonged duration of action. According to the invention, it was surprisingly found that the HAS-antiarrhythmic conjugates have a significantly longer in vivo plasma half-life and that the activity of the active ingredients is not adversely affected to a significant extent by coupling to HAS.

According to the present invention, any antiarrhythmic active ingredient can be used for the preparation of the conjugates. The active ingredient can be selected from the group consisting of sodium channel blockers, beta-receptor blockers, selective repolarization prolonging active ingredients, calcium antagonists and local anesthetics. Preferably, the active ingredient is adenosine, quinidine, procainamide, disopyramide, lidocaine, phenytoin, mexiletine, ajamaline, Parjmalium, propafenone, atenolol, propanolol, amiodarone, sotalol, verapamil, gallopamil or diltiazem, wherein the use of adenosine is particularly preferred.

According to an embodiment of the present invention, coupling between the antiarrhythmic active ingredient and the HAS takes place via the reducing end groups of the HAS.

When adenosine is used, this active ingredient can for example be bound to the HAS via the amino group, wherein a coupling between the amino group of the adenosine and the reducing end group of the HAS is particularly preferred. A coupling variant, wherein native adenosine is present after metabolisation (separating off the HAS) is preferred.

As an alternative, the active ingredient can be coupled to the HAS via a so-called linker.

The present invention further relates to pharmaceutical compositions comprising one of the compounds according to the invention. Generally, the pharmaceutical composition further comprises a pharmaceutically compatible carrier, and it can be formulated, for example, for intravenous application.

Finally the invention relates to the use of the compounds according to the invention for the preparation of a medicament for the treatment of arrhythmia, in particular for the treatment of ventricular arrhythmia.

According to an alternative embodiment, the invention relates to the use of a compound according to the invention for the preparation of a medicament for the induction of apoptosis, for example in tumor tissues or in inflammatory tissues.

The present invention relates to compounds comprising a conjugate of HAS and an antiinfective active ingredient or an antibiotic, respectively, as well as their use for the treatment of infectious diseases.

The penetration of microorganisms (viruses, bacteria, fungi, protozoa) into a macroorganism (plant, animal, human) and the propagation in this macroorganism is called infection. Formation and course of an infectious disease substantially depend on pathogenicity of the microorganism and immunity of the macroorganism.

For decades, antiinfective active ingredients have been used as chemotherapeutics in order to fight infectious diseases.

A. Flemings identified Penicillin already in 1928 by the active ingredient's characteristic to form staphylococci-free areas on culture plates. Penicillin was the first antibiotic that was obtained on an industrial scale, and it gained great importance in clinical practice.

Today, active ingredients from a group of β-lactam antibiotics which are produced from a fungus of the species *Penicillium* (for example, *P. chrysogenum* and *P. notatum*) are designated as penicillins. The bacteriocidal effect is based on blocking the synthesis of the bacterial cell wall. The penicillin inactivates the bacterial enzyme transpeptidase, thereby preventing cross-linking of the polysaccharide chains of the cell wall murein.

Since the discovery, numerous active ingredients were isolated and synthesized which inhibit the growth of microorganisms or kill microorganisms. Most antibiotics originate from *Streptomyces* species (approximately 65%) which were isolated from soil. It is assumed that these substances are used by the microorganism to suppress competitors in the soil.

The number of isolated antibiotics is estimated to be approximately 8000, approximately 100 thereof can be used in the field of medicine. A classification of the active ingredients into different substance classes was performed according to different aspects, for example chemical structure or mode of action.

Meanwhile, antibiotics are approved not only for fighting infectious diseases, but also as immuno depressants, cytostatics in anti-tumor therapy, plant protectives, for the preservation of foods, as fattening auxiliary agent in the feeding of animals, etc.

In recent years, numerous strains of microorganisms occurred which are resistant to antibiotics. In addition to single-resistant strains, multi-resistant strains were frequently found which complicates fighting of certain diseases.

When studying the activity of different antibiotics against certain pathogens, it was found that several of the active ingredients, for example amoxycillin or ampicillin, almost exclusively act extracellularly (Scaglione et al., Chemotherapie, Vol. 39 (1993), 416-423; Balland et al., J. Antimicrob. Chemother. Vol. 37 (1996), 105-115, the disclosures of which are hereby incorporated by reference). Therefore, these active ingredients cannot be used against microorganisms which primarily are present inside the cell. Ampicillin-nanoparticles have been produced in order to improve the intracellular activity (e.g. Balland et. al., see above).

For infections such as tuberculosis or other infections caused by mycobacteria, broadening of the spectrum of treatment possibilities would be desirable due to the combination therapy which is always required. In view of other intracellular infections such as chlamydia infection, for which the potential importance for the pathogenesis of arteriosclerosis was only recently discovered (Stille and Dittmann, Herz, Vol. 23 (1998), p. 185- 192, hereby incorporated by reference), intracellular antibiotics with a depot effect could represent an important progress in therapy and prophylaxis.

According to the invention, it was now surprisingly found that coupling of antiinfective active ingredients to HAS results in improved pharmacokinetic characteristics of the active ingredients, in particular in a prolonged in vivo half-life, an improved intracellular uptake and/or effect of the active ingredient.

According to the invention, any antiinfective ingredient or antibiotic, respectively, can be used. Preferably, an active ingredient is selected from the group consisting of amino penicillins, cephalosporines, amino cephalosporines, beta-lactam-antibiotics, carbapenems, amino glycosides, tetracyclines, macrolide antibiotics, gyrase inhibitors, glycopeptide antibiotics, lincomycins, streptogramins, everninomicins, oxazolidinones, nitroimidazoles, sulfonamides, co-trimoxazol, local antibiotics, virustatics, antimycotics, tuberculostatics.

It may for example be ampicillin, amoxicillin, cefotaxim, ceftazidim, vancomycin, clindamycin, metronidazol, isoniazid, rifampicin, rifabutin, rifapentin, ethambutol, pyracinamide, streptomycin, prothionamide, or dapsone, wherein the use of an amino penicillin, such as ampicillin, amoxycillin, macrolide or of streptomycin is particularly preferred.

According to one embodiment of the present invention, an amino penicillin is used as an active ingredient which is directly and covalently coupled to the hydroxyethyl starch via the amino group of the amino penicillin.

According to another embodiment, an amino cephalosporin is used instead of the amino penicillin, thereby achieving a reduced allergenicity. As further embodiments, macrolide-HAS couplings may be used, wherein erythromycin or a derivative thereof is used, in particular erythromycylamin. As an alternative, streptomycin can be used as active ingredient.

According to a particularly preferred embodiment of the present invention, the coupling between the antiinfective active agent and the hydroxyethyl starch may take place via the reducing end groups of the hydroxyethyl starch.

In accordance with a further embodiment of the present invention, the antiinfective active agent is coupled to the hydroxyethyl starch via a linker.

The present invention further comprises pharmaceutical compositions, which comprise a compound according to the invention. Usually, the pharmaceutical compositions further comprise a pharmaceutically compatible carrier.

Finally, the present invention relates to the use of one of the compounds according to the invention for the preparation of a medicament for the treatment of an infectious disease. The pharmaceutical composition may in particular be suitable for the treatment of infectious diseases which, amongst others, are caused by intracellular pathogens. These may originate from the complete spectrum of pathogenics and facultative pathogenics, for example bacterial, viral or parasitic pathogens, mycoplasms, mycobacteria, chlamydia, rickettsia, etc.

In a further aspect of the present invention, HAS-nucleic acid conjugates are provided. Presently, nucleic acid libraries are screened in large scale for nucleic acids which have a desired activity. For example, a respective activity can be the ability of a nucleic acid to bind to certain other nucleic acids, receptors or viral proteins. This binding may be stimulated or inhibited by a biological signal. For this purpose, in addition to naturally occurring D-DNA and D-RNA molecules, also L-DNA and L-RNA molecules are used which differ from the naturally occurring molecules in that they contain L-ribose or L-deoxyribose instead of the corresponding D-forms as components of the nucleic acid (e.g. WO 98/08856, hereby incorporated by reference). In the context of the present invention, it was shown that HAS-nucleic acid conjugates can be prepared which may retain their natural function (e.g. Example 7).

The present invention further provides processes for the preparation of covalent HAS-active ingredient conjugates. The processes can be performed in an aqueous or organic reaction medium, wherein carrying out the coupling in an aqueous medium is preferred.

Thus, processes for the preparation of a covalent HAS-active ingredient conjugate are provided in which HAS and at least one active ingredient are reacted with each other in a reaction medium. The reaction medium is characterized in that it is water or a mixture of water with an organic solvent, which comprises at least 10 weight-% water.

The reaction medium of the process according to the invention comprises at least 10 wt.-%, preferably at least 50 wt.-%, in particular at least 80 wt.-%, such as for example 90 wt.-%, or even up to 100 wt.-%, water, and accordingly up to 90 wt.-%, preferably up to 50 wt.-%, in particular up to 20 wt.-%, for example 10 wt.-%, or even up to 0 wt.-%, organic solvent. The reaction takes place in an aqueous phase. The preferred reaction medium is water.

The process according to the invention is already advantageous because toxicologically unacceptable solvents need not necessarily be used, and thus, with the product prepared according to the invention, the removal of even small residues of toxicologically unacceptable solvents which is always necessary according to the known process in order to avoid the undesired contamination with solvent is dispensed with. Furthermore, the additional quality control necessary according to the process known in the art for residues of toxicologically harmful solvents can be omitted because the process according to the invention favors the use of toxicologically acceptable solvents. Solvents preferred according to the invention are for example toxicologically harmless protic solvents such as ethanol or propylene glycol.

Furthermore, it is an advantage of the process according to the invention that irreversible or reversible structural changes of proteins or peptides induced by organic solvents, which cannot be systematically excluded in processes in organic solvents, are basically avoided. The product obtained with the process according to the invention is consequently different from that prepared in DMSO.

According to the invention it was, furthermore, surprisingly found that a coupling of HAS to active ingredients can be carried out in an aqueous solution without secondary reactions being observed to a significant extent. The process according to the invention thus leads directly to improved products of great purity. The process according to the invention thus makes possible for the first time the simple preparation of HAS-active ingredient conjugates in which the active ingredient is present in active form and the advantageous properties of the HAS are retained. No particular processes are necessary to isolate the HAS-active ingredient conjugate from the reaction mixture as the reaction takes place in the aqueous phase, i.e. organic solvents need not necessarily be purified off.

According to the invention it is preferred that HAS binds directly to a ε-NH$_2$-group, α-NH$_2$-group, SH-group, COOH group or —C(NH$_2$)$_2$-group of the active ingredient. Alternatively, a further reactive group can be introduced into HAS or the bond between HAS and the active ingredient can take place via a linker. The use of the corresponding linkers for the binding of active ingredients to PEG is known in the state of the art. The use of amino acids, in particular glycine, alanine, leucine, isoleucine, and phenylalanine, as well as hydrazine and oxylamine derivatives as linkers, as disclosed in WO 97/38727 and EP 605 963, the disclosures which are hereby incorporated by reference, is preferred.

According to one embodiment of the process of the present invention, HAS is oxidized before binding to the active ingredient. The oxidation can take place according to one of the processes known in the state of the art, a selective oxidation of the reducing end groups of HAS being preferred. This facilitates processes in which the oxidized reducing end group of the HAS reacts with an amino group of the active ingredient resulting in the formation of an amide. This embodiment has the particular advantage that a specific bond between HAS and the active ingredients, and thus a particularly homogeneous product, is achieved.

HAS can be reacted with oxidized reducing end groups and the active ingredient preferably for at least 12, most preferably at least 24 hours. Furthermore, it can be desirable to add any activator, for example ethyldimethyl-aminopropyl-carbodiimide (EDC). The molar ratio between HAS and the active ingredient during the reaction can be randomly selected, but is normally in the range of HAS:active ingredient of 20:1 to 1:20, a ratio of 6:1 to 1:6 being particularly preferred. The best results were achieved with a molar ratio of HAS:active ingredient of approx. 2:1.

Other coupling reactions between an amino group of the active ingredient and HAS are naturally also comprised in the scope of the invention, for example, processes in which HAS and the active ingredient are reacted directly with each other, a Schiff's base forming between HAS and active ingredient as intermediate product. The azomethin group —CH═N— of the Schiff's base can then be reduced with formal addition of <2H> to a methyleneamine group —CH$_2$—NH—. For this reduction, a person skilled in the art can use a number of reduction agents known in the state of the art, reduction using BH$_4$ is particularly preferred.

The HAS can be coupled with any group of the active ingredient. The coupling is preferably carried out such that the conjugate displays at least 50%, preferably at least 75% of the activity of the active ingredient before coupling, a retention of at least 95% of the activity being particularly preferred. The coupling reaction can naturally also be controlled such that the HAS is bound exclusively to one or more specific groups of the active ingredient, for example to lysine or cysteine residues of a peptide. Particular advantages result if HAS is bound to one or more specific groups of active ingredient via the oxidized reducing end groups, as homogenous HAS-active ingredient conjugates are obtained with a corresponding process.

According to a preferred embodiment of the process of the present invention, HAS and a protein or a peptide are used as starting substances for the reaction. Any therapeutic or diagnostic proteins of natural or recombinant origin can be used. A list of the active ingredients of recombinant preparation currently on the market is to be found in Pharma Business, July/August 2000, pages 45 to 60. The present invention comprises the preparation of HAS-active ingredient conjugates which comprise any one of the active ingredients named in this publication.

The preparation of conjugates using cytokines, for example interferons, interleukins, growth factors, enzymes, enzyme inhibitors, receptors, receptor fragments, insulin, factor VIII, factor IX, antibiotics (or antiinfectives), peptide antibiotics, viral coat proteins, haemoglobins, erythropoietin, albumins, hTPA, antibodies, antibody fragments, single-chain antibodies, DNA, RNA or a derivative thereof is particularly preferred. Particular advantages result when using recombinant proteins or peptides in the process according to the invention. As already stated, corresponding proteins can often not be used as active ingredients due to their properties being antigenic for humans. After coupling to HAS by the processes according to the invention, however, the immunogenicity of the recombinant proteins decreases, which allows the medical use on humans.

Furthermore, particular advantages result upon coupling of HAS to proteins having a short chain and smaller peptides. Currently, a large number of peptide libraries are being produced, for example, phage display libraries wherein short oligopeptides (for example 3 to 20 mers) are expressed on the surface of phages. Furthermore, antibodies from a single polypeptide chain (so-called "single chain antibodies") are expressed in bacteria or on the surface of phages. These libraries are screened for specific active ingredient or binding activity. Hitherto, the therapeutic and diagnostic use of corresponding peptide active ingredients or antibodies has however failed because these are very quickly excreted from the organism due to their small size (e.g. Chapman et al., 1999, loc. cit.). With the process according to the invention, these peptides can advantageously be coupled to HAS and have an in vivo half-life which allows to use the same as an active ingredient.

As an alternative to the above embodiment, a hormone, a steroid hormone, a hormone derived from amino acids or a hormone derived from fatty acids can be used as active ingredient. In the specific case, it may be necessary to introduce an active group into the hormone before binding to HAS, for example by using a linker.

According to the invention, any physiologically compatible HES can be used as starting material. HES with an average molecular weight (weight average) of 1 to 300 kDA, in particular of 1 to 150 kDa is preferred. HES with an average molecular weight of 2 to 40 kD is particular preferred. HES preferably has a molar degree of substitution of 0.1 to 0.8 and a ratio of C$_2$:C$_6$ substitution in the range of 2 to 20, in each case relative to the hydroxyethyl groups.

The invention furthermore relates to the HAS-active ingredient conjugates obtainable according to the above processes. These conjugates have advantageous properties, namely high activity of the active ingredient, low immunogenicity, long residence time in the body and excellent Theological properties, which increase the medicinal benefit of the conjugates.

Accordingly, the present invention likewise comprises processes for preparing a medicament or diagnostic in which a HAS-active ingredient conjugate is prepared according to one of the above processes and mixed with a pharmaceutically compatible carrier, adjuvant or auxiliary known in the state of the art, as well as medicaments or diagnostics obtainable according to this process.

The medicinal use of the corresponding medicament depends on the type of active ingredient used. If, for example, haemoglobin is used as active ingredient, the conjugate can be used as an oxygen transport agent. If on the other hand, a cytokine is used as active ingredient for the preparation, the conjugate can for example be used in tumor therapy. The concentration of the conjugate to be used in each case in the medicament can be ascertained immediately in dose-effect tests by any average person skilled in the art.

The diagnostics can be used in vivo or in vitro to diagnose illnesses or disorders. If an antibody or antibody fragment is used as active ingredient, the conjugate is suitable, for example, for carrying out the ELISA detection processes customary in the state of the art.

In the examples, the materials described in the following were used:

| | |
|---|---|
| Human serum albumin: | Sigma-Aldrich A3782 |
| HES 130 kD: | Type 130/0.5, prepared from T91SEP (Fresenius Kabi) |
| Data: | $M_w$: 130 000 ± 20 000 D |
| $M_n$: | 42 600 D |
| HES 10 kD: | Type HHH 4-2 (Fresenius Kabi) |
| Data: | $M_w$: 9 800 D |
| $M_n$: | 3 695 D |
| EDC: (ethyldimethyl aminopropyl carbodiimide) | Sigma-Aldrich no. 16.146-2 |
| HOBt (1-hydroxy-1H-benzotriazolhydrate) | Sigma-Aldrich no. 15.726-0 |
| DIG glycan detection kit: | Roche-Boehringer no. 1142 372 | diaminobutane are simply examples of the active ingredients defined above. Example 7 describes the coupling of oligonucleotides to HES.

EXAMPLE 1

Selective Oxidation of the Reducing end Groups of the Hydroxyethyl Starch

For the selective oxidation of the reducing end groups of the hydroxyethyl starch (130 kD and 10 kD), the same were dissolved in a minimal quantity of water and reacted with different quantities of an iodine solution and a KOH solution.

The mixture was stirred until the colour indicating $I_2$ disappeared. This procedure was repeated several times in order to achieve the addition of a larger quantity of the iodine solution and KOH solution. The solution was subsequently purified using an Amberlite IR 120 Na+ cation-exchanger resin, dialysed for 20 hours against distilled water (dialysis tube with an exclusion limit of 4-6 kD) and lyopholized.

The degree of oxidation was determined in each case using the process disclosed in Somogyi, N. (Method in Carbohydride Chemistry, Vol. 1, (1962) p. 384-386, hereby incorporated by reference). The protocols of the oxidation reaction are reproduced in Table 1.

TABLE 1

Oxidation of the reducing end groups of the HES (130 kD and 10 kD) under different conditions

| Error! Bookmark not defined.Error! Bookmark not defined. Process{T C\11 "Process"} | HES (Mn) | Iodine solution 0.1 N | KOH solution 0.1 N | Solvent | Reaction time | Yield |
|---|---|---|---|---|---|---|
| OXIDATION (1) HES 130 | 1 g $2.4 \times 10^{-5}$ mol | 0.3 ml $3.0 \times 10^{-5}$ mol | 0.5 ml $5.0 \times 10^{-5}$ mol | Water 4.0 ml | 4 hours 25° C. | 30.1% |
| OXIDATION (2) HES 130 | 4 g $9.4 \times 10^{-5}$ mol | 1.0 ml $1.0 \times 10^{-4}$ mol | 1.5 ml $1.5 \times 10^{-4}$ mol | Water 6.0 ml | overnight 25° C. | 24.8% |
| OXIDATION (3) HES 130 | 5 g $1.2 \times 10^{-4}$ mol | 1.2 ml $1.2 \times 10^{-4}$ mol | 1.5 ml $1.5 \times 10^{-4}$ mol | Water 7.5 ml | overnight 25° C. | 24.3% |
| OXIDATION (4) HES 130 | 5 g $1.2 \times 10^{-4}$ mol | 3.0 ml $3.0 \times 10^{-4}$ mol | 4.5 ml $4.5 \times 10^{-4}$ mol | Water 7.5 ml | overnight 25° C. | 60.8% |
| OXIDATION (5) HES 130 | 5 g $1.2 \times 10^{-4}$ mol | 4.0 ml $4.0 \times 10^{-4}$ mol | 5 ml $5.0 \times 10^{-4}$ mol | Water 7.5 ml | overnight 25° C. | 80.0% |
| OXIDATION (6) HES 130 | 8 g $1.9 \times 10^{-4}$ mol | 7.0 ml $7.0 \times 10^{-4}$ mol | 11.5 ml $1.2 \times 10^{-3}$ mol | Water 7.5 ml | overnight 25° C. | 88.4% |
| OXIDATION (7) HES 130 | 10 g $2.4 \times 10^{-4}$ mol | 10 ml $1.0 \times 10^{-3}$ mol | 20 ml $2.0 \times 10^{-3}$ mol | Water 7.5 ml | overnight 25° C. | 100% |
| OXIDATION (1) HES 10 | 5 g $1.4 \times 10^{-3}$ mol | 2.0 ml $2.0 \times 10^{-4}$ mol | 2.0 ml $2.0 \times 10^{-4}$ mol | Water 10.0 ml | 20 hours 25° C. | 3.0% |
| OXIDATION (2) HES 10 | 5 g $1.4 \times 10^{-3}$ mol | 3.5 ml $3.5 \times 10^{-4}$ mol | 4.5 ml $4.5 \times 10^{-4}$ mol | Water 10.0 ml | overnight 25° C. | 5.3% |
| OXIDATION (3) HES 10 | 15 g $4.1 \times 10^{-3}$ mol | 21.0 ml $2.1 \times 10^{-3}$ mol | 31.0 ml $3.1 \times 10^{-3}$ mol | Water | overnight 25° C. | 10.5% |
| OXIDATION (4) HES 10 | 8 g $2.2 \times 10^{-3}$ mol | 83.0 ml $8.3 \times 10^{-3}$ mol | 180.0 ml $1.8 \times 10^{-2}$ mol | Water | overnight 25° C. | 80.0% |
| OXIDATION (5) HES 10 | 7 g $1.9 \times 10^{-3}$ mol | 95.0 ml $9.5 \times 10^{-3}$ mol | 210.0 ml $2.1 \times 10^{-2}$ mol | Water | overnight 25° C. | 100.0% |
| OXIDATION (6) HES 10 | 6.4 g $1.7 \times 10^{-3}$ mol | 50 ml $5.0 \times 10^{-3}$ | 150 ml $1.5 \times 10^{-2}$ mol | Water | overnight 25° C. | 100.0% |

The following examples 1 to 6 describe the coupling of HSA and diaminobutane to HES with oxidized reducing end groups or the direct coupling of HSA to HES. HSA and The protocols summarized in this table are reproduced in detail in the following for the oxidation (6), HES 10 kD: 6.4 g HES 10kD (1.7 mmol) were dissolved in a reaction vessel accompanied by continuous stirring in a few ml water. 50 ml of a 0.1 N iodine solution (5.0 mmol) and 150 ml of a 0.1 N KOH solution (15 mmol) were added. This mixture was left to stand overnight at 25° C. The mix was purified with Amberlite IR 120 (Na+ form) and dialysed against water (cellulose acetate dialysis tube; Cut-off 4 to 6 kD). The dialysed product was lyophilized (Heraeus-Christ Alpha, flask-drying overnight).

As can be inferred from Table 1, a complete oxidation of the reducing end groups (corresponds to a yield of 100%) of the HES 130 kD was achieved, after the iodine quantity was increased from $3.0 \times 10^{-5}$ mol to $1.0 \times 10^{-3}$ ml.

For a complete oxidation of the reducing end groups of the HES 10kD, a further increase of the iodine quantity to a concentration of more than $2.1 \times 10^{-3}$ was necessary.

EXAMPLE 2

Binding of HES with Oxidized Reducing end Groups to HSA in the Aqueous Phase

For the coupling, hydroxyethyl starch with oxidized reducing end groups (ox-HES) and HSA were completely dissolved in water. When the solution was clear, EDC dissolved in water was added. After activation by EDC accompanied by moderate stirring, further quantities of EDC were added. Where appropriate, the reaction was activated with HOBt and left to stand overnight. The product was purified for 15 hours by dialysis against distilled water and subsequently lyophylized (called Process A in the following).

The protocols of the coupling reaction are in Table 2.

The coupling reaction VII between ox-HES 130 kD and HSA is explained in detail in the following: In a round-bottomed flask, 130 mg ox-HES 130 kD (degree of oxidation approx. 100%) and 100 mg HSA were dissolved accompanied by stirring in approx. 5 ml water at room temperature. As soon as the solution was clear, 200 mg EDC in 3 portions, each dissolved in 5-10 ml water, were added over a period of one hour. Between each addition, the reaction mixture was stirred at room temperature for about 4 hours. After 24 hours reaction time, the mixture was dialysed against water (cellulose acetate dialysis tube; Cut-off 4 to 6 kD). The product was then lyophilized.

EXAMPLE 3

Direct Binding of HES to HSA in the Aqueous Phase

The principle of this reaction is based on the formation of Schiff's bases between HES and amino groups of the protein, the reaction being controlled through the reaction of the Schiff's bases to the corresponding amine by $NaBH_4$ (called Process B in the following).

For this, HES was dissolved completely in a small amount of water. To this end, HSA dissolved in borate buffer, pH 9.0, was added. $NaBH_4$ was added to this solution and the whole left at room temperature accompanied by stirring. A further aliquot of HES 130 kD, followed by further $NaBH_4$, was added. After the reaction was finished, dialysis and freeze-drying was carried out as described.

The protocols of the individual tests are summarized in Table 3.

TABLE 2

Coupling reactions between HES (130 kD and 10 kD) with oxidized reducing end groups and HSA under different conditions (Process A; number in brackets in the HES column reproduces the oxidation process according to Table 1).

| Process A | HSA | ox-HES (Mn) | EDC | HOBt | Solvent | Activation | Reaction |
|---|---|---|---|---|---|---|---|
| Coupling I | 300 mg | 100 mg (1) | 25 mg | 100 mg | H₂O/dioxane | 1.5 hours | 4 hours |
| ox-HES 130 | $4.4 \times 10^{-6}$ mol | $2.4 \times 10^{-6}$ mol | $1.6 \times 10^{-4}$ mol | $7.7 \times 10^{-4}$ mol | 13 ml/2 ml | 3–4° C. | 25° C. |
| Coupling II | 100 mg | 300 mg (2) | 15 mg | 100 mg | H₂O/dioxane | 1.5 hours | overnight |
| ox-HES 130 | $1.5 \times 10^{-6}$ mol | $7.0 \times 10^{-6}$ mol | $9.7 \times 10^{-5}$ mol | $7.7 \times 10^{-4}$ mol | 10 ml/3 ml | 3–4° C. | 25° C. |
| Coupling III | 200 mg | 3.8 g (5) | 46.5 mg | 20 mg | H₂O/dioxane | 0 hours | 24 hours |
| ox-HES 130 | $3.0 \times 10^{-6}$ mol | $8.9 \times 10^{-5}$ mol | $3.0 \times 10^{-4}$ mol | $1.5 \times 10^{-4}$ mol | 10 ml/3 ml | | 25° C. |
| Coupling IV | 100 mg | 1.9 g (5) | 25 mg | 20 mg | Water | 1.5 hours | overnight |
| ox-HES 130 | $1.5 \times 10^{-6}$ mol | $4.5 \times 10^{-5}$ mol | $1.6 \times 10^{-4}$ mol | $1.5 \times 10^{-4}$ mol | | 3–4° C. | 25° C. |
| Coupling V | 200 mg | 4.3 g (5) | 100 mg | 0 mg | Water | 0 hours | overnight |
| ox-HES 130 | $3.0 \times 10^{-6}$ mol | $1.0 \times 10^{-4}$ mol | $6.0 \times 10^{-4}$ mol | | | | 25° C. |
| Coupling VI | 100 mg | 130 mg (7) | 50 mg | 0 mg | Water* | 0 hours | 5 hours |
| ox-HES 130 | $1.5 \times 10^{-6}$ | $3.0 \times 10^{-6}$ mol | $3.0 \times 10^{-4}$ mol | | 5 ml + 10 ml | | 25° C. |
| Coupling VII | 100 mg | 130 mg (7) | 200 mg | 0 mg | Water* | 0 hours | 24 hours |
| ox-HES 10 | $1.5 \times 10^{-6}$ | $3.0 \times 10^{-6}$ mol | $3.0 \times 10^{-4}$ mol | | 5 ml + 2 × 10 ml | | 25° C. |
| Coupling I | 100 mg | 300 mg (1) | 5 mg | 100 mg | H₂O/dioxane | 1.5 hours | overnight |
| ox-HES 10 | $1.5 \times 10^{-6}$ mol | $8.1 \times 10^{-5}$ mol | $3.0 \times 10^{-5}$ mol | $7.7 \times 10^{-4}$ mol | 13 ml/2 ml | 3–4° C. | 25° C. |
| Coupling II | 70 mg | 1.0 g (2) | 15.5 mg | 0 mg | Water | 10 ml | overnight |
| ox-HES 10 | $1.0 \times 10^{-6}$ mol | $2.7 \times 10^{-4}$ mol | $1.0 \times 10^{-4}$ mol | | | 0 hours | 25° C. |
| Coupling III | 200 mg | 2.0 g (3) | 77.5 mg | 20 mg | Water | 0 hours | 6 hours |
| ox-HES 10 | $3.0 \times 10^{-6}$ mol | $8.1 \times 10^{-4}$ mol | $5.0 \times 10^{-4}$ mol | $1.5 \times 10^{-4}$ mol | | | 25° C. |
| Coupling IV | 50 mg | 7.4 g (4) | 282 mg | 0 mg | Water | 0 hours | overnight |
| ox-HES 10 | $7.4 \times 10^{-7}$ mol | $2.0 \times 10^{-3}$ mol | $1.5 \times 10^{-3}$ mol | | | 25° C. | |
| Coupling V | 100 mg | 103 g (6) | 93 mg | 0 mg | Water* | 0 hours | 20 hours |
| ox-HES 10 | $1.5 \times 10^{-6}$ mol | $2.8 \times 10^{-5}$ mol | $5.6 \times 10^{-4}$ mol | | 4 ml | | 25° C. |
| Coupling VI | 100 mg | 103 g (6) | 200 mg | 0 mg | Water* | 0 hours | 30 hours |
| ox-HES 10 | $1.5 \times 10^{-6}$ mol | $2.8 \times 10^{-5}$ mol | $1.2 \times 10^{-3}$ mol | | 3 × 5 ml | | 25° C. |

*= Addition of the EDC solution with a dropping funnel within 60 minutes

TABLE 3

Direct coupling between HES (130 kD and 10 kD) and HSA under different conditions (Process B).

| Process B | HSA | HES (Mn) | NaBH4 | Buffer pH | Reaction time |
|---|---|---|---|---|---|
| COUPLING I  | 50 mg | 500 mg | 500 mg | Na$_2$HPO$_4$, 0 ml | 48 hours |
| HES 130 | $7.5 \times 10^{-7}$ mol | $1.2 \times 10^{-5}$ mol | $1.3 \times 10^{-2}$ mol | 7.4 | 25° C. |
| COUPLING II | 100 mg | 1.0 g | 60 mg | Na$_2$HPO$_4$, 1 ml | 20 hours |
| HES 130 | $1.5 \times 10^{-6}$ mol | $2.4 \times 10^{-5}$ mol | $1.6 \times 10^{-3}$ mol | 7.4 | 25° C. |
| COUPLING III | 50 mg | 9.8 g | 285 mg | Na$_2$HPO$_4$, 1 ml | 36 hours |
| HES 130 | $7.5 \times 10^{-7}$ mol | $2.3 \times 10^{-4}$ mol | $7.5 \times 10^{-3}$ mol | 7.4 | 25° C. |
| COUPLING IV | 50 mg | 2.0 g | 180 mg | Borate 0.1M | 30 hours |
| HES 130 | $7.5 \times 10^{-7}$ mol | $4.7 \times 10^{-5}$ mol | $4.7 \times 10^{-3}$ mol | 7.4 | 25° C. |
| COUPLING V | 50 mg | 4.0 g | 60 mg | Borate 0.1M | 100 hours |
| HES 130 | $7.5 \times 10^{-7}$ mol | $9.4 \times 10^{-5}$ mol | $1.6 \times 10^{-3}$ mol | 7.4 | 25° C. |
| COUPLING I | 50 mg | 2.8 g | 28 mg | Borate 0.1M | 80 hours |
| HES 10 | $7.5 \times 10^{-7}$ mol | $9.4 \times 10^{-5}$ mol | $1.6 \times 10^{-3}$ mol | 9.0 | 25° C. |

In detail, for the coupling of the HES 130 kD, 2.0 g of this compound were completely dissolved in water (approx. 5 ml). 50 mg of HSA dissolved in 1 ml 0.1 M borate buffer, pH 9.0 were added. 30 mg NaBH$_4$ were added to this solution and the whole left at room temperature accompanied by stirring. After 18 h, a further aliquot of 2.0 g HES 130 kD, followed by a further 30 mg NaBH$_4$, were added. After 100 h reaction time in total, dialysis and freeze-drying were carried out (coupling V, HES 130 kD).

For the coupling of the HES 10 kD, 1.4 g of this compound were completely dissolved in water (approx. 5 ml). 50 mg of HSA dissolved in 1 ml 0.1 M borate buffer, pH 9.0, were added. 14 mg NaBH$_4$ were added to this solution and the whole left at room temperature accompanied by stirring. After 18 hours a further aliquot of 1.4 g HES 10 kd, followed by a further 14 mg NaBH$_4$, was added. After a total of 80 hours reaction time, dialysis and freeze-drying were carried out (coupling I, HES 10 kD).

EXAMPLE 4

Analysis of the Coupling Products Using GPC

The reaction products were first analyzed using gel-permeation chromatography (GPC)

Figure 2:
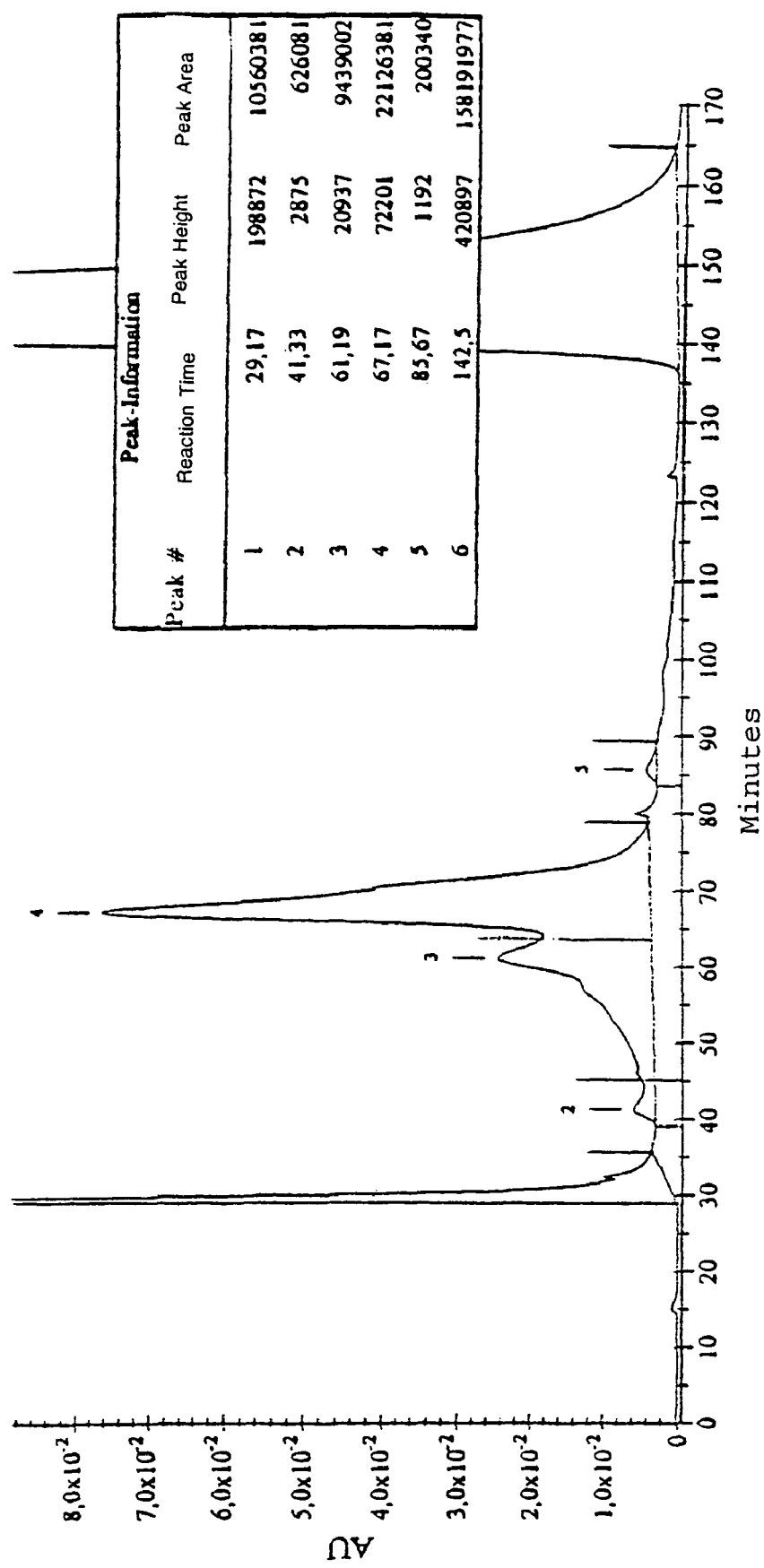
FIG. 2 GPC chromatogram of the coupling reaction between ox-HES 130 kD and HSA according to process A.IV.
Figure 3:
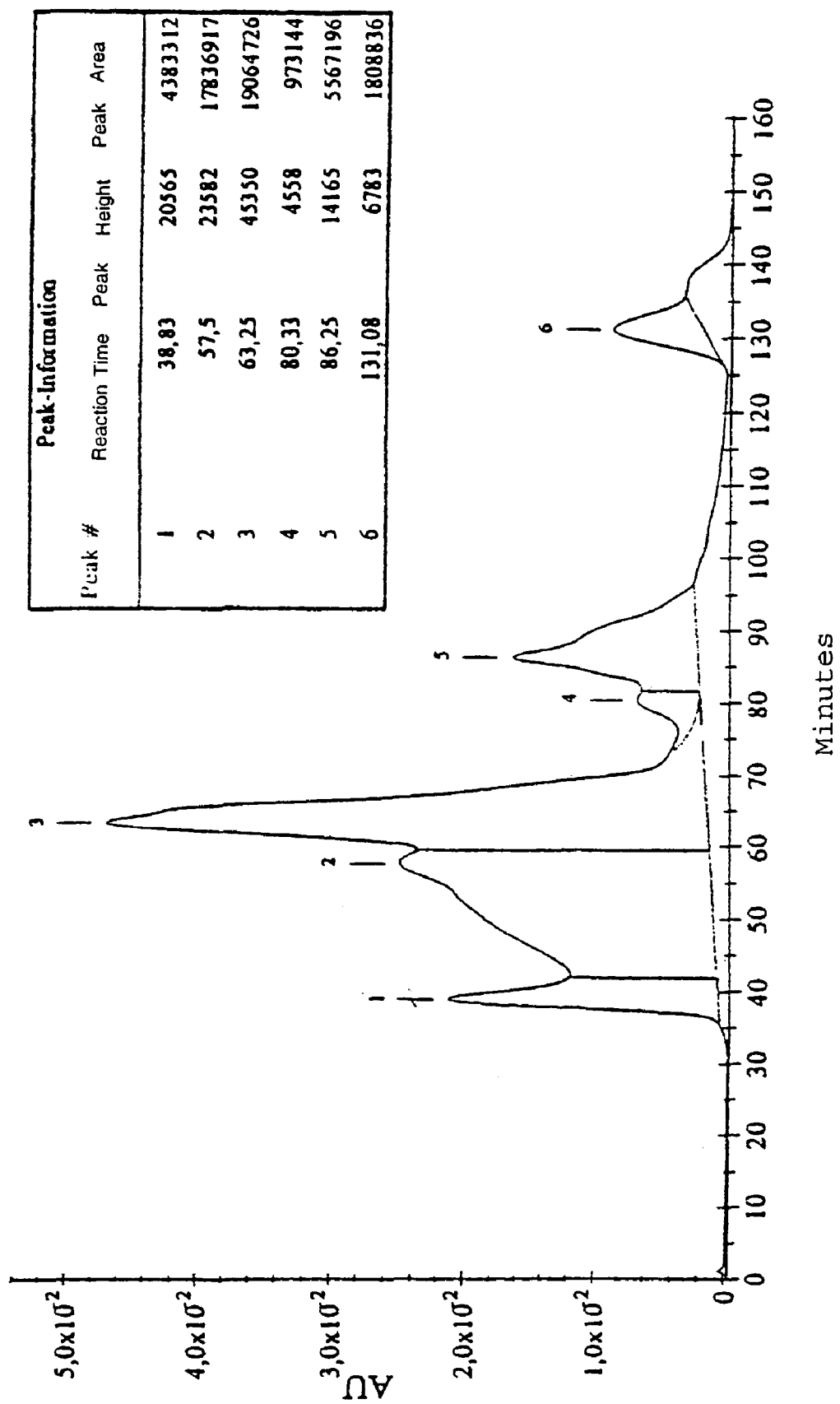
FIG. 3 GPC chromatogram of the coupling reaction between ox-HES 130 kD and HSA according to process A.V. and with a reaction time of 2 hours.
Figure 4:
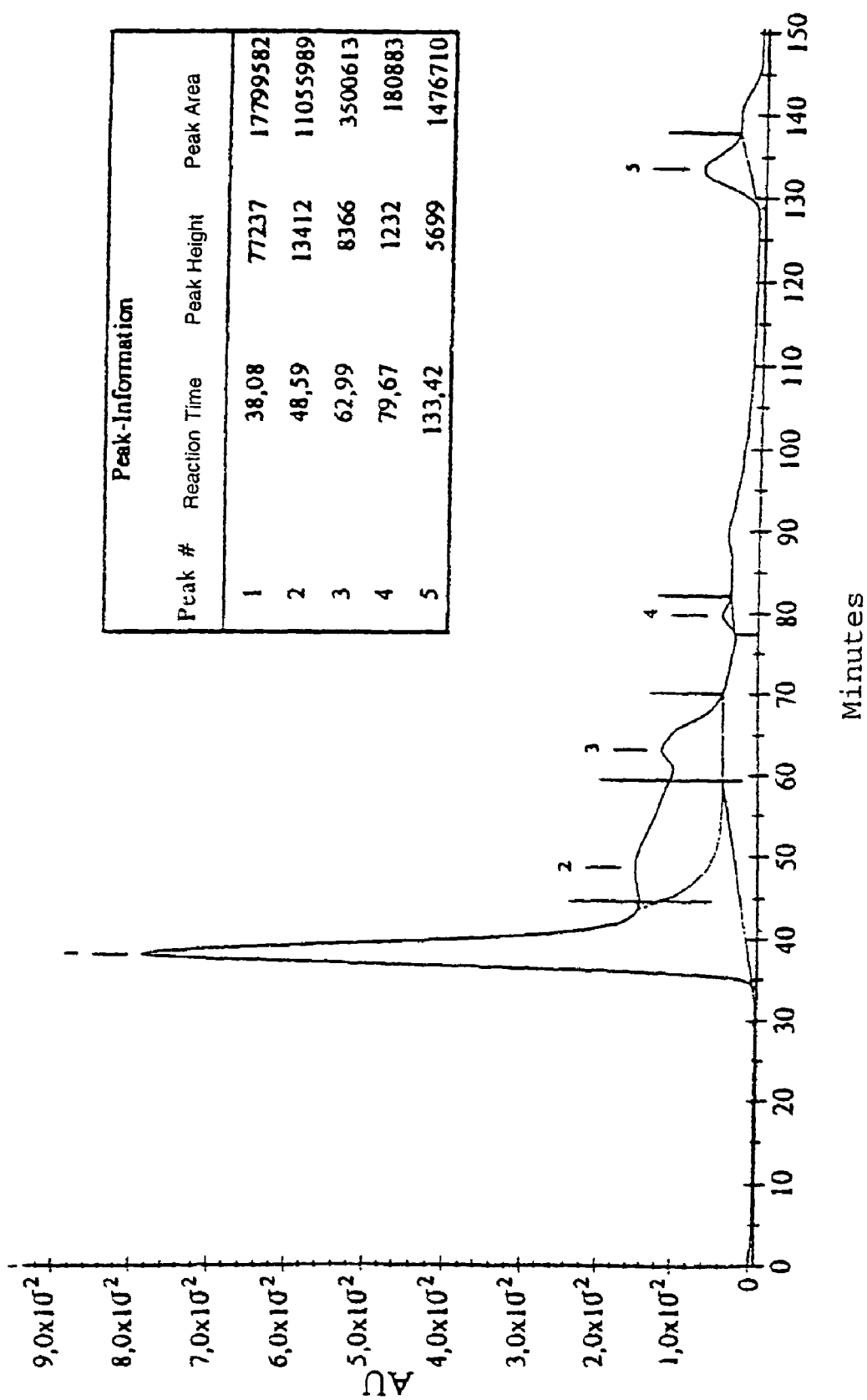
FIG. 4 GPC chromatogram of the coupling reaction between ox-HES 130 kD and HSA, process A.V., reaction time overnight.
Figure 5:
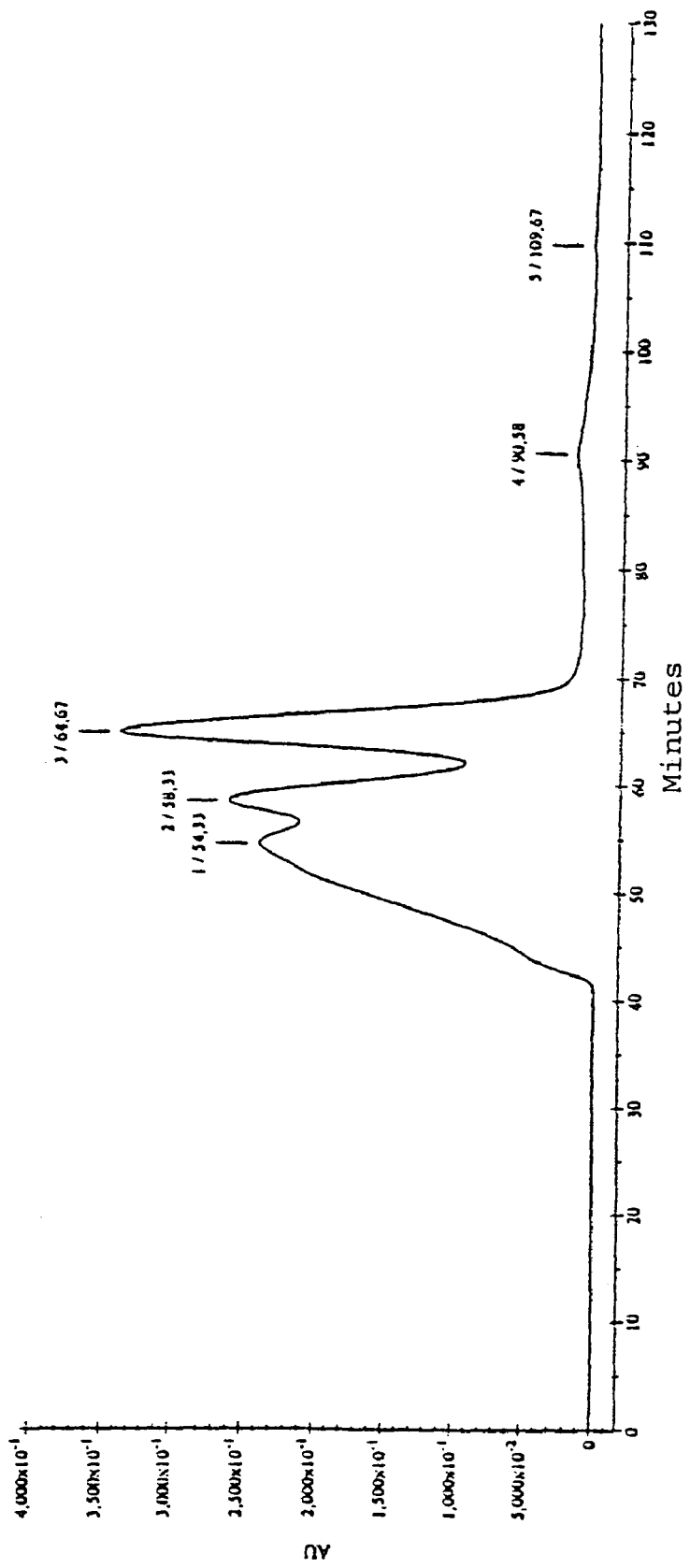
FIG. 5 GPC chromatogram of the coupling reaction between ox-HES 10 kD and HSA according to process A.V, after 2 hours (FIG. 5a) and overnight (FIG. 5b)
Figure 6:
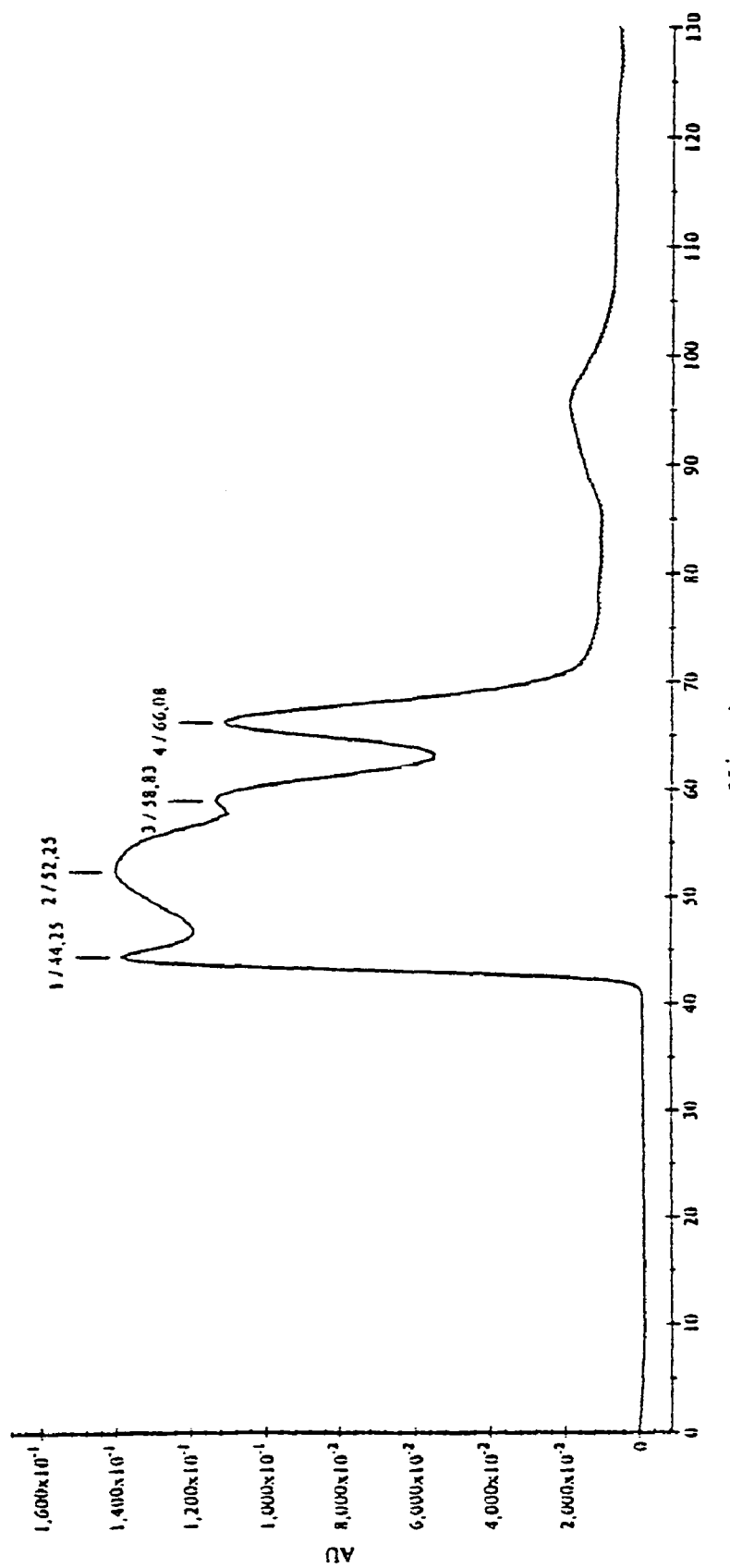
FIG. 6 GPC chromatogram of the coupling reaction between ox-HES 130 kD and HSA according to process A.VII, after 24 hours reaction time.
Figure 7:
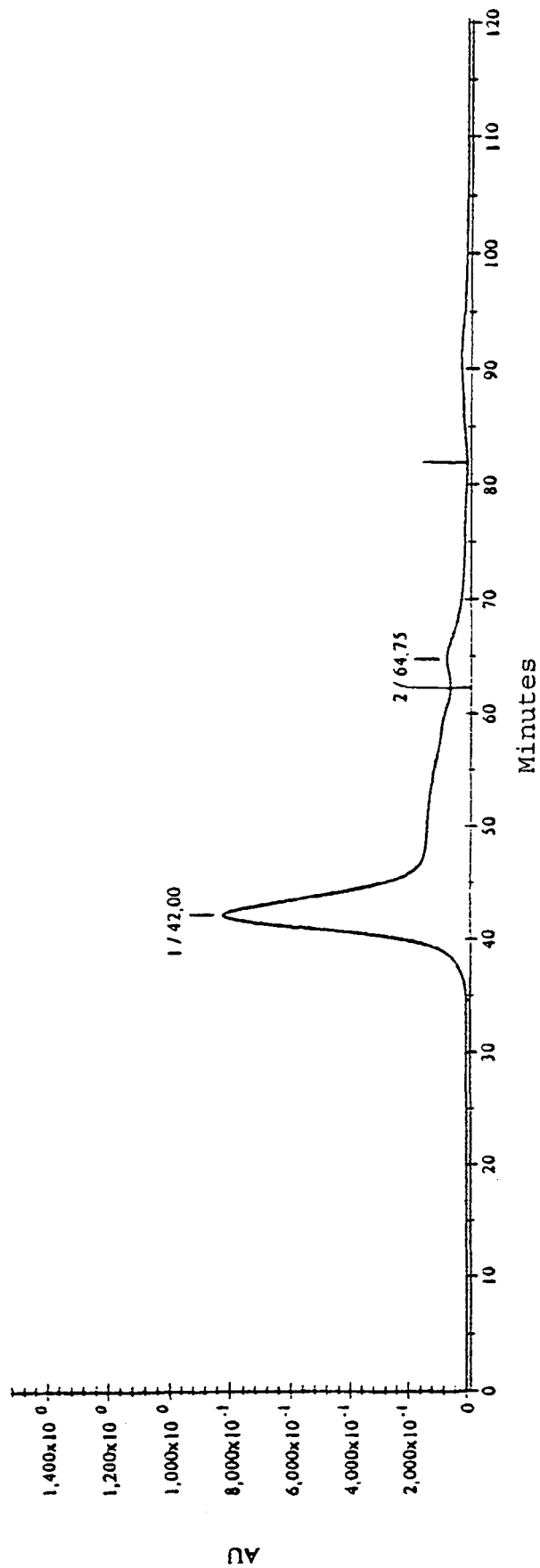
FIG. 7 GPC chromatogram of the coupling reaction between ox-HES 130 kD and HSA according to process B.V.

4.1 An FPLC device (Pharmacia) which was connected to a HPLC UV monitor (Hitachi) was used for the GPC. Furthermore, the following conditions were used:
Column: Superose 12 HR 10/30 (1×30 cm) (Pharmacia)
UV monitor: 280 nm
Pump: 0.2 ml/min
Buffer: 50 mM phosphate/150 mM NaCl pH 7.2.
Under these conditions, the HSA peak is normally found after 63 minutes, a small peak, which is caused by HSA dimers, also being able to be measured at approx. 57 minutes. The chromatograms obtained by means of GPC can be analyzed as follows:
4.2 FIG. 1 is a chromatogram which shows the size distribution of the products after coupling of ox-HES 130 kD to HSA (coupling III). With this coupling process, very good results were achieved without HOBt activation. A clear, single broad peak was measured at 37 minutes and a further, smaller band at 45 minutes, which indicates a coupling product with higher molecular weight than HSA. At the same time, traces of non-modified HSA were found.
FIG. 2 shows the size distribution of the products after coupling of ox-HES 130 kD to HSA (coupling IV). The reaction was activated with HOBt. It is shown that this activation reduces the yield, possibly by encouraging secondary reactions.
FIGS. 3 and 4 show the size distribution of the reaction products during and after the coupling reaction of ox-HES 130 kD to HSA (coupling V). After 2 hours reaction time, non-modified HSA was found as the product with the highest concentration, but in addition the first coupling products with a higher molecular weight were found. After the reaction was finished, a homogeneous coupling product with a retention time of approx. 35 minutes was found in high concentration. Non-modified HSA and other coupling products were present in relatively low concentration.
FIG. 5 shows the corresponding size distribution of the reaction products during and after the coupling reaction of ox-HES 10 kD to HSA (coupling V). Here too, it is shown that the concentration of the coupling products with a molecular weight which lies above the weight of HSA increases in the course of the reaction.
Finally, a coupling reaction in which almost all HSA molecules were able to be transferred into a homogenous coupling product is shown in FIG. 6 (reaction products of coupling VII).
4.3 An example of the chromatograms which were obtained upon analysis of the direct coupling of HES to HSA is shown in FIG. 7 (Process B, HES 130 kD, coupling V). A significant peak was identified at approx. 65 minutes (HSA). In addition, however, a coupling product was also shown (peak at approx. 42 minutes).

EXAMPLE 5

Analysis of the Coupling Products by Means of SDS-PAGE and Western Blot 5.1 PAGE was carried out in the presence of sodium dodecyl sulfate (SDS) using a Miniprotean II device from Biorad and 7.5% acrylamide gels. Electrophoresis was carried out as per the manufacturers instructions. The gels were stained with silver using the Blum process (Elektrophoresis, Vol. 8, (1997) p. 93-99), to make proteins visible.

The presence of glycans in the coupling products was detected by means of Western-Blot and Glycan-Detections-Kit from Roche-Boehringer. After separation of the products by means of SDS-PAGE, these were transferred to a nitrocellulose membrane using the blotting apparatus of the Miniprotean II electrophoresis unit. The membrane was then oxidized using periodate under conditions in which only the vicinal OH groups are oxidized. These were then reacted with an amino-functionalized digoxigenin. Bound digoxigenin was detected by means of specific monoclonal antibodies which were bound to an alkaline phosphatase. For this, a substrate of the phosphatase (4-nitro-tetrazolium chloride/5-bromo-4-chloro-3-indolylphosphate) was added, which produces a difficultly soluble blue-violet product. This product precipitates onto the membrane and thus renders the bands visible. Non-modified HSA and creatinase were used as negative controls whilst transferrin served as positive control.

The exact process steps are described in the instruction leaflet enclosed with this kit (Roche-Boehringer).

Figure 8:
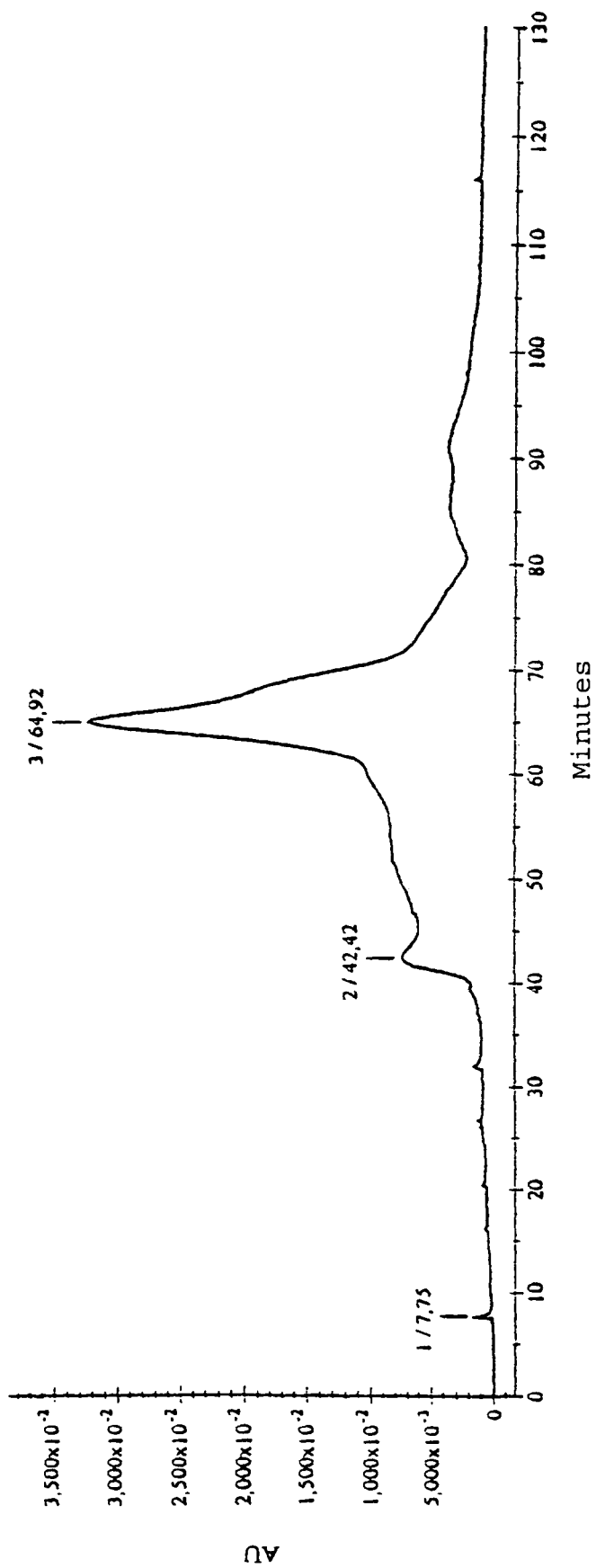
FIG. 8 SDS-PAGE and Western Blot of different coupling reactions between HES and HSA.
Figure 9:
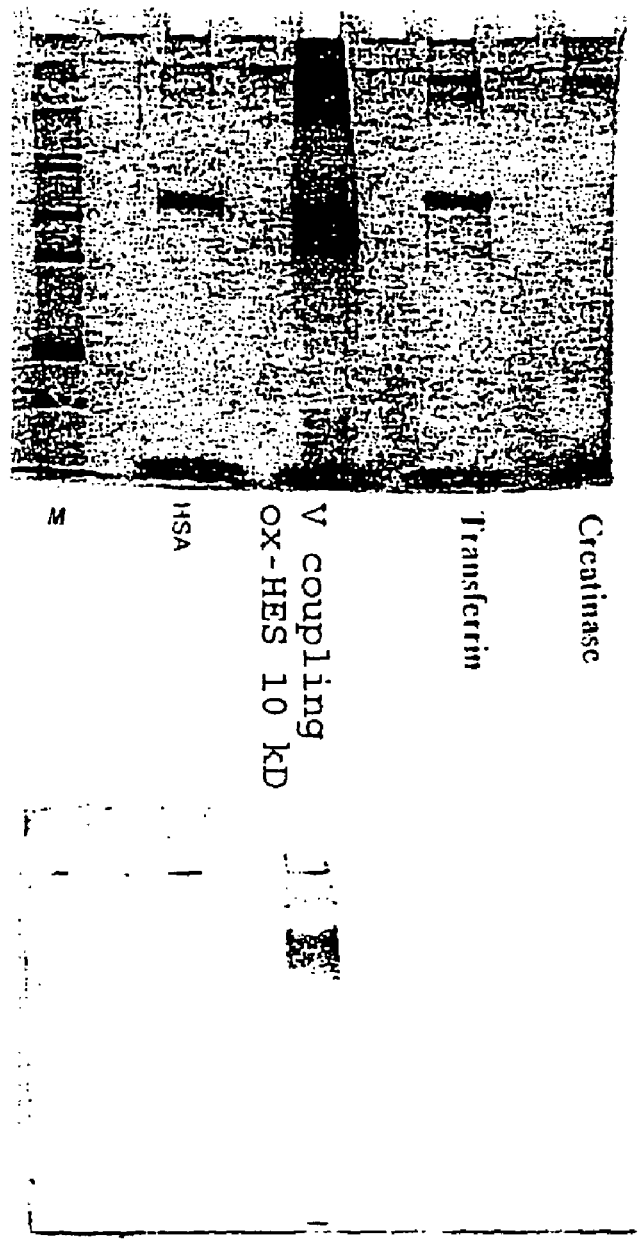
FIG. 9 SDS-PAGE and Western Blot of different coupling reactions between HES and HSA.

5.2 FIGS. 8 and 9 each show a picture of the silver-stained SDS-PAGE gel (top) and the picture of the corresponding products after transfer onto a membrane and glycan detection (bottom). As can be inferred from these figures, a relatively homogeneous glycan forms as a reaction product during the coupling reaction, whilst at the same time the concentration of non-modified HSA decreases.

EXAMPLE 6

Analysis of Potential Secondary Reactions

To determine whether secondary reactions in the form of a self-condensation of HES with oxidized reducing end groups occur, the following reaction mixtures were prepared:

SMCC 4 to form conjugate 5. SMCC 4 which has not reacted is separated by centrifugation using a centrifugation/dialysis unit. The maleimid-group of conjugate 5 subsequently reacts with the thiol group of the thio-DNA 1 to the desired product 6. The region in 6, which is marked in bold mererly represents a spacer and can have any form.

Evaluation of the biological activity of conjugate 6 was performed via restriction with the restriction enzyme EcoR1. Restriction enzymes only cleave double-stranded DNA with an intact recognition sequence.

DNA:

Double-stranded DNA synthesized by MWG Biotech Corporation, Ebersberg, Germany, was used. The sequences of the single strands are:

```
SEQ ID NO. 1:
5'-GTAGAGACAGGAGGCAGCAGTTGAATTCGCAGGGTGAGTAGCAGTAG
AGC-3';

SEQ ID NO: 2:
5'-GCTCTACTGCTACTCACCCTGCGAATTCAACTGCTGCCTCCTGTCTC
TAC-3';
``` modified with 5'thiol C6 S—S by MWG (e.g. FIG. 10).

TABLE 4

Reaction mixtures for the analysis of secondary reactions

| | ox-HES | EDC | HOBt | Water | Reaction time |
|---|---|---|---|---|---|
| HES 130 kD | 500 mg<br>$1.2 \times 10^{-5}$ mol | 15 mg<br>$7.8 \times 10^{-5}$ mol | — | 5.0 ml | 30 hours<br>25° C. |
| HES 130 kD | 500 mg<br>$1.2 \times 10^{-5}$ mol | 15 mg<br>$7.8 \times 10^{-5}$ mol | Saturated solution | 5.0 ml | 30 hours<br>25° C. |
| HES 10 kD | 100 mg<br>$2.7 \times 10^{-5}$ mol | 3.4 mg<br>$1.8 \times 10^{-5}$ mol | — | 5.0 ml | 30 hours<br>25° C. |
| HES 10 kD | 100 mg<br>$2.7 \times 10^{-5}$ mol | 3.4 mg<br>$1.8 \times 10^{-5}$ mol | saturated solution | 5.0 ml | 30 hours<br>25° C. |
| HES 130 kD | 700 mg<br>$1.6 \times 10^{-5}$ mol | 31 mg<br>$1.6 \times 10^{-4}$ mol | — | 5.0 ml | 30 hours<br>25° C. |
| HES 130 kD | 700 mg<br>$1.6 \times 10^{-5}$ mol | 31 mg<br>$1.6 \times 10^{-4}$ mol | Saturated solution | 5.0 ml | 30 hours<br>25° C. |

The aim of the experiments was to demonstrate the extent to which a potential self-condensation of HES takes place in the presence or absence of HOBt. The samples were lyophilized and forwarded to Fresenius-Kabi for the carrying out of the analysis.

By means of GPC and light-scatter measurements, within the detection limits of a few percent, no indications of increases in molecular weight were found.

EXAMPLE 7

Coupling of Oxidized HES to DNA and Analysis of the Functionality of the Coupling Products Reaction Principle:

A schematic representation of the reaction can be found in FIG. 10. In a first step, the amino group of the amine-HES12KD 3 reacts with the N-hydroxysuccinimid group of Both DNA single strands were dissolved in bidest. Water in a concentration of 2 µg/µl, and were hybridized in a ratio of 1:1 at 96° C. to a double-stranded thio-DNA 1 with a concentration of 2 µg/µl.

Analysis of the Products:

Analysis was performed by a gel electrophoresis on a 4% agarose gel with a TBE running buffer consisting of 45 mM Tris borate, 1 mM EDTA, pH 8.0, using 1 µg DNA in the presence of 50 µg ethidium bromide per 100 ml gel in each case. The images were taken by use of a CCD-system modular (INTAS Imaging Instruments, Göttingen, Germany) and an UV transilluminator UVT-20 S/M/L (Herolab, Wiesloch, Germany) at 312 nm.

1 µl (1 µg DNA) of the reaction mix were taken and cleaved with 1 µl (20 U) EcoR1 restriction enzyme (New England Biolabs, Schwalmbach/Taunus, Germany), 1 µl reaction buffer (50 mM sodium chloride, 100 mM Tris HCl, 10 mM magnesium chloride, 0.025% Triton X-100, pH 7,5 from New England Biolabs) and 7 μl bidest. water at 37° C. for 3 hours.

Modification of HES

Oxidation of HES12KD (Fresenius, Lot 2540SR2.5P) with an average molecular weight of 12.000 g/mol with iodine solution to oxo-HES12KD 2 was performed according to the process disclosed in DE 196 28 705, hereby incorporated by reference.

Reaction of 1,4-diaminobutane with oxo-HES12KD 2:

1.44 g (0.12 mmol) of oxo-HES12KD 2 were dissolved in water-free dimethyl sulfoxide (DMSO), added dropwise to a solution of 1.5 ml (1.50 mmol)-1,4 diaminobutane under nitrogen, and stirred at 40° C. for 19 hours. The reaction mixture was added to a mixture of 80 ml ethanol and 80 ml aceton. The precipitate formed was separated by centrifugation and resuspended in 40 ml water. The solution was dialyzed for 4 days against water (SnakeSkin dialysis tube, 3.5 KD cut off, Perbio Science Deutschland, Bonn, Germany) and subsequently lyophilized. The yield was 80% (1.06 g) amino-HES12 KD 3.

Coupling of amino-HES12KD 3 to thio-DNA 1.

Figure 11:
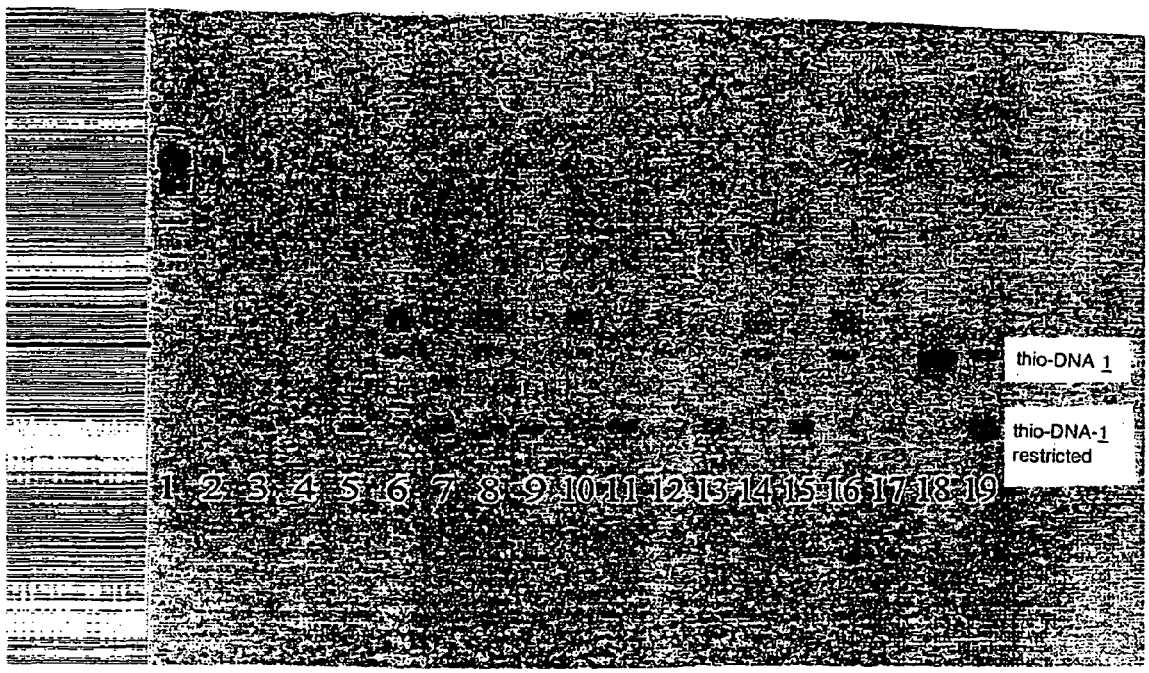
FIG. 11 image of a gel showing the HES-DNA conjugate prior to and after digestion with a restriction enzyme.

1 mg SMCC 4 dissolved in 50 μl water-free DMSO were added to 400 μl of a 10 mg/ml-solution of amino-HES12KD 3 in a buffer of 10 mM sodium phosphate and 150 mM sodium chloride, pH 7.44, and the mixture was incubated 80 min at room temperature and 10 min at 46° C. Subsequently, the mixture was centrifuged, the supernatant was removed from the precipitate, and it was again cetrifuged. 200 μl of the supernatant were taken and centrifuged for 45 minutes at 14000 g with a MICROCON® YM-3 (Amicon, Millipore Co., Eschborn, Germany) centrifugation-dialysis unit. After the addition of 400 μl buffer consisting of 10 mM sodium phosphate and 150 mM sodium chloride, pH 7.44, it was again centrifuged for 45 minutes. Additional 400 μl buffer were added, and it was centrifuged for 60 minutes. The amount of conjugate solution which was left in the dialysis unit was filled up to 50 μl. 10 μl of this solution were added to 10 μl of thio-DNA solution 1 and both were reacted with each other for 14 hours at room temperature. 1 μl was taken for analysis. FIG. 11 shows the results in lanes 2 and 3.

The reaction conditions for the described experiment and for experiments with modified reaction conditions are summarized in Table 1. The results are depicted in FIG. 11.

Summary of the Results:

The following conditions were analyzed:
1. Amount of SMCC: 1 mg (lanes 2, 6, 10, 14) or 5.6 mg (lanes 4, 8, 12, 16), respectively;
2. Temperature for the reaction with thio-DNA 1: room temperature (lanes 2, 4, 6, 8) or 37° C. (lanes 10, 12, 14, 16), respectively;
3. Buffer conditions:
   10 mM phosphate, 150 mM sodium chloride without EDTA, pH 7.44 (lanes 2, 4, 10, 12) or 100 mM phosphate, 150 mM sodium chloride+50 mM EDTA, ph 7.23 (lanes 6, 8, 14, 16), respectively.

In FIG. 11, lanes 2-18 represent the results of the 8 coupling experiments of amino-HES12KD 3 to thio-DNA 1 using SMCC. The results directly from the reaction or after the reaction and subsequent digestion of the DNA, respectively, are depicted next to each other. In lane 1, a mixture of different reference DNAs is loaded as length marker. Lanes 18 and 19 show thio-DNA 1 or digested thio-DNA 1, respectively. In addition to non-reacted thio-DNA 1, all experiments show coupling products at higher masses (lanes 2, 4, 6, 8, 10, 12, 14, 16). Since HES12KD is a mixture of molecules of different size, the coupling products also show a molecular weight distribution. All coupling products contain intact DNA as they can be completely digested by EcoR1. This is also demonstrated by nearly complete vanishing of corresponding diffuse bands after digestion (lanes 3, 5, 7, 9, 11, 13, 15, 17).

TABLE 1

Reaction conditions of the coupling of amino-HES12KD 3 to thio-DNA 1

| Lane | Experiment | Temp. [° C.] | SMCC [mg] | DNA | HES12KD | Buffer | |
|---|---|---|---|---|---|---|---|
| 1 | Marker | | | | | | |
| 2 | 19A1 | RT | 1 | thio-DNA | amino-HES12KD | 7.44, 10 mM | |
| 3 | | | | | | | digested |
| 4 | 19B1 | RT | 5.6 | thio-DNA | amino-HES12KD | 7.44, 10 mM | |
| 5 | | | | | | | digested |
| 6 | 19C1 | RT | 1 | thio-DNA | amino-HES12KD | 7.23, 100 mM | |
| 7 | | | | | | | digested |
| 8 | 19D1 | RT | 5.6 | thio-DNA | amino-HES12KD | 7.23, 100 mM | |
| 9 | | | | | | | digested |
| 10 | 19A2 | 37° C. | 1 | thio-DNA | amino-HES12KD | 7.44, 10 mM | |
| 11 | | | | | | | digested |
| 12 | 19B2 | 37° C. | 5.6 | thio-DNA | amino-HES12KD | 7.44, 10 mM | |
| 13 | | | | | | | digested |
| 14 | 19C2 | 37° C. | 1 | thio-DNA | amino-HES12KD | 7.23, 100 mM | |
| 15 | | | | | | | digested |
| 16 | 19D2 | 37° C. | 5.6 | thio-DNA | amino-HES12KD | 7.23, 100 mM | |
| 17 | | | | | | | digested |
| 18 | | | | thio-DNA | | | |
| 19 | | | | | | | digested |

The invention claimed is:

1. A method for preparing a conjugate comprising a hydroxyalkyl starch (HAS), said method comprising: providing HAS with a selectively oxidized reducing end and an active ingredient; and selectively reacting the HAS with the active ingredient to form a conjugate comprising HAS covalently linked via the oxidized reducing end to the active ingredient, the reaction occurring in a reaction medium comprising at least 10%/weight of water, wherein said reaction medium is water or a mixture of water with a water-miscible organic solvent.

2. The method according to claim 1, wherein said active ingredient is selected from the group consisting of vitamins, vaccines, toxins, antibiotics, antiarrythmics, appetite suppressants, anesthetics, analgesics, antirheumatics, antiallergics, antiasthmatics, antidepressives, antidiabetics, antihistames, antihypertonics, antineoplastic compounds, alkylating agents, antimetabolites, sodium channel blockers, P-receptor blockers, selective enhancers of repolarisation, calcium antagonists, local anesthetics, aminopenicillins, cephalosporins, aminocephalosporine, beta-Lactam-antibiotics, carbapeneme, aminoglycoside, tetracycline, macrolide-antibiotics, gyrase-inhibitors, glycopeptide-antibiotics, lincomycine, streptogramine, everninomicin, oxazolidinone, nitroimidazole, sulfonamide, local antibiotics, virustatics, antimycotics, and tuberculostatics.

3. The method according to claim 1, wherein said active ingredient is selected from the group consisting of a hormone, a steroid, a lipid, a protein, an oligopeptide, a polypeptide, and a nucleic acid.

4. The method according to claim 3, wherein said nucleic acid is a D- or L-nucleic acid.

5. The method according to claim 1, wherein said active ingredient is selected from the group consisting of an enzyme, enzyme-inhibitor, receptor, receptor fragment, insulin, factor VIII, factor IX, cytolune, interferon, interleukin, growth factor, peptide antibiotic, viral coat protein, hemoglobin, erythropoietin, albumin, hTPA, antibody, antibody-fragment, single chain-antibody, a steroid hormone, a hormone derived from amino acids or a hormone derived from fatty acids, mitomycin C, cyclophosphamide, bleomycin, chlorambucil, cisplatin, ara-C, fludarabine, doxorubicin, etoposide, 5-FU, MTX, vinblastine, vincristine, vindesine, hydroxyurea, 6-MP, CCNU, adenosine, chinidin, procaine amide, diisopyramide, lidocaine, phenytoin, mexiletine, ajamaline, parjmalium, propafenon, atenolol, propanolol, amiodaron, sotalol, verapamil, gallopamil, diltiazem, ampicillin, amoxicillin, cefotaxime, ceftazidime, vancomycin, clindamycin, metronidazole, isoniazide, rifampicin, rifabutin, rifapentin, ethambutol, pyrazinamide, streptomycin, prothionamide, and dapson.

6. The method according to claim 1, wherein said active ingredient includes at least one functional group selected from the group consisting of an ε-$NH_2$-group, an α-$NH_2$-group, a SH group, a COOH group, and a —$C(NH_2)_2$-group, and wherein said oxidized HAS is linked to said at least one functional group.

7. The method according to claim 1, wherein said selectively oxidized reducing end group of said oxidized HAS reacts with an amino group of said active ingredient to result in the formation of an amide.

8. The method according to claim 1, wherein said active ingredient that is provided is bound to a cross-linker, and wherein said conjugate comprises HAS covalently linked via said cross-linker to the active ingredient.

9. The method according to claim 1, wherein said oxidized HAS that is provided is bound to a cross-linker, and wherein said conjugate comprises HAS covalently linked via said cross-linker to the active ingredient.

10. The method according to claim 1, wherein said oxidized HAS is a hydroxyethyl starch (HES) having an average molecular weight of 1 to 300 kDa.

11. The method according to claim 1, wherein said oxidized HAS is a HES having an average molecular weight of 2 to 40 kDa.

12. The method according to claim 1, wherein said oxidized HAS is a HES having a molar degree of substitution of 0.1 to 0.8 and having a ratio of C2:C6 substitution in the range from 2 to 20, for each hydroxyethyl group.

13. The method of claim 1, wherein the organic solvent is ethanol, propylene glycol, or dioxane.

14. The method of claim 1, wherein said reaction medium is water.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Synthesized

<400> SEQUENCE: 1
gtagagacag gaggcagcag ttgaattcgc agggtgagta gcagtagagc           50

<210> SEQ ID NO 2
<211> LENGTH: 50
<212> TYPE: DNA
<213> ORGANISM: Artificial Sequence
<220> FEATURE:
<223> OTHER INFORMATION: SyntheSized

<400> SEQUENCE: 2
gctctactgc tactcaccct gcgaattcaa ctgctgcctc ctgtctctac           50
```